(12) United States Patent
Ferrari et al.

(10) Patent No.: US 7,078,026 B2
(45) Date of Patent: Jul. 18, 2006

(54) STRUCTURED COMPOSITION BASED ON SILICONE OIL, ESPECIALLY FOR COSMETIC USE

(75) Inventors: Véronique Ferrari, Maisons-Alfort (FR); Jean Mondet, Aulnay Sous Bois (FR)

(73) Assignee: L'Oreal S.A., Paris (FR)

( * ) Notice: Subject to any disclaimer, the term of this patent is extended or adjusted under 35 U.S.C. 154(b) by 174 days.

(21) Appl. No.: 10/170,549

(22) Filed: Jun. 14, 2002

(65) Prior Publication Data

US 2003/0068348 A1 Apr. 10, 2003

Related U.S. Application Data

(60) Provisional application No. 60/299,744, filed on Jun. 22, 2001.

(30) Foreign Application Priority Data

Jun. 14, 2001 (FR) .............................. 01 07778

(51) Int. Cl.
*A61K 7/48* (2006.01)

(52) U.S. Cl. .................. 424/78.02; 424/63; 424/64; 424/65; 424/69; 424/70.7; 424/78.03; 510/136

(58) Field of Classification Search ............. 424/78.02, 424/78.05, 63, 64, 65, 69, 70.7, 401; 510/136
See application file for complete search history.

(56) References Cited

U.S. PATENT DOCUMENTS

| | | | |
|---|---|---|---|
| 2,823,195 | A | 2/1958 | Shorr et al. |
| 3,723,566 | A | 3/1973 | Thompson et al. |
| 4,322,400 | A | 3/1982 | Yuhas |
| 5,262,505 | A | 11/1993 | Nakashima et al. |
| 5,407,986 | A | 4/1995 | Furukawa et al. |
| 5,412,004 | A | 5/1995 | Tachibana et al. |
| 5,473,041 | A | 12/1995 | Itoh |
| 5,567,428 | A | 10/1996 | Hughes |
| 5,725,882 | A | 3/1998 | Kuman et al. |
| 5,837,223 | A | 11/1998 | Barone et al. |
| 5,874,069 | A | 2/1999 | Mendolia et al. |
| 5,919,441 | A | 7/1999 | Mendolia et al. |
| 5,981,680 | A | 11/1999 | Petroff et al. |
| 5,985,297 | A | 11/1999 | Mellul et al. |
| 6,045,782 | A | 4/2000 | Krog et al. |
| 6,051,216 | A | 4/2000 | Barr et al. |
| 6,060,072 | A | 5/2000 | Konik et al. |
| 6,103,250 | A | 8/2000 | Brieva et al. |
| 6,353,076 | B1 | 3/2002 | Barr et al. |
| 6,362,287 | B1 | 3/2002 | Chorvath et al. |
| 6,362,288 | B1 | 3/2002 | Brewer et al. |
| 6,423,324 | B1 | 7/2002 | Murphy et al. |
| 6,426,062 | B1 | 7/2002 | Chopra et al. |
| 6,451,295 | B1 | 9/2002 | Cai et al. |
| 6,503,632 | B1 | 1/2003 | Hayashi et al. |
| 6,524,598 | B1 | 2/2003 | Sunkel et al. |
| 6,541,017 | B1 | 4/2003 | Lemann et al. |
| 6,569,955 | B1 | 5/2003 | Brewer et al. |
| 2002/0048557 | A1 | 4/2002 | Cai et al. |
| 2003/0068348 | A1 | 4/2003 | Ferrari et al. |
| 2003/0072730 | A1 | 4/2003 | Tournilhac |
| 2003/0082129 | A1 | 5/2003 | Buckingham et al. |
| 2003/0170188 | A1 | 9/2003 | Ferrari et al. |
| 2003/0232030 | A1 | 12/2003 | Lu et al. |
| 2003/0235548 | A1 | 12/2003 | Lu et al. |
| 2003/0235552 | A1 | 12/2003 | Yu |
| 2003/0235553 | A1 | 12/2003 | Hansenne et al. |
| 2004/0001799 | A1 | 1/2004 | Lu et al. |
| 2004/0115153 | A1 | 6/2004 | Yu |
| 2004/0115154 | A1 | 6/2004 | Yu |
| 2004/0120912 | A1 | 6/2004 | Yu |
| 2004/0126336 | A1 | 7/2004 | Hansenne et al. |
| 2004/0170586 | A1 | 9/2004 | Ferrari et al. |
| 2004/0180032 | A1 | 9/2004 | Manelski et al. |
| 2005/0020769 | A1 | 1/2005 | Lu et al. |

FOREIGN PATENT DOCUMENTS

| | | |
|---|---|---|
| EP | 0 377 447 A2 | 7/1990 |
| EP | 0 693 517 A1 | 1/1996 |
| EP | 0 923 928 | 6/1999 |
| EP | 1 048 686 | 11/2000 |
| EP | 1 068 856 | 1/2001 |
| FR | 2 765 800 | 1/1999 |
| GB | 134 8783 | 3/1974 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO 01/09239 A1 | 2/2001 |
| WO | WO 01/97758 A2 | 12/2001 |
| WO | WO 02/17870 | 3/2002 |
| WO | WO 02/17871 | 3/2002 |
| WO | WO 02/089760 A1 | 11/2002 |
| WO | WO 03/013447 A2 | 2/2003 |
| WO | WO 03/105788 A2 | 6/2003 |

OTHER PUBLICATIONS

English Language Derwent Abstract of EP 0 923 928, Jun. 23, 1999.
English Language Derwent Abstract of EP 1 068 856, Jan. 17, 2001.
English Language Derwent Abstract of FR 2 765 800, Jan. 15, 1999.

*Primary Examiner*—Jyothsna Venkat
(74) *Attorney, Agent, or Firm*—Oblon, Spivak, McClelland, Maier & Neustadt, P.C.

(57) ABSTRACT

A physiologically acceptable composition, especially a cosmetic composition, comprising a liquid fatty phase comprising at least one silicone oil, structured with at least one polymer chosen from homopolymers and copolymers with a weight-average molecular mass ranging from 500 to 500 000, comprising at least one moiety comprising:
  at least one polyorganosiloxane group comprising from 1 to 1 000 organosiloxane units in the chain of the moiety of in the form of a graft, and
  at least two groups capable of establishing hydrogen interactions,
the polymer being solid at room temperature and soluble in the liquid fatty phase at a temperature of from 25 to 250° C., and solid particles having a hydrophobic surface.

102 Claims, No Drawings

STRUCTURED COMPOSITION BASED ON SILICONE OIL, ESPECIALLY FOR COSMETIC USE

This application claims priority of U.S. Provisional Application No. 60/299,744, filed Jun. 22, 2001.

The present invention relates to a care and/or treatment and/or makeup composition for the skin, including the scalp, and/or the lips of human beings, which comprises a liquid fatty phase comprising at least one silicone oil, gelled with a specific polymer, which can be provided in the form of a cast makeup product and in the form of a makeup stick, such as lipsticks, the application of which can produce a glossy and migration-resistant deposit.

The invention further relates to cosmetic and dermatological compositions, such as, makeup products, which have staying power, transfer-resistance and stability properties.

It is commonplace, in cosmetic or dermatological products, to find a structured, namely gelled and/or rigidified, liquid fatty phase; this is particularly the case in solid compositions, such as deodorants, lip balms, lipsticks, eyeshadows, concealer products and cast foundations. This structuring is obtained with the aid of waxes or fillers. Unfortunately, these waxes or fillers have a tendency to make the composition matt, which is not always desirable, such as for a lipstick.

In accordance with the invention, the phrase "liquid fatty phase" is understood to mean a fatty phase, which is liquid at room temperature (25° C.) and atmospheric pressure (760 mmHg), and which comprises one or more fatty substances that are liquid at room temperature, also known as oils, which are compatible with one another and comprise a silicone oil.

In accordance with the present invention, the phrase "structured liquid fatty phase" is understood to mean that this structured phase does not run between the fingers and is at least thickened.

The structuring of the liquid fatty phase makes it possible to limit its exudation from solid compositions, and furthermore, to limit, after deposition on the skin or the lips, its migration into the wrinkles and fine lines, which is desired for a lipstick or an eyeshadow. Significant migration of the liquid fatty phase, laden with colouring materials, leads to an unaesthetic effect around the lips or the eyes, which can accentuate the wrinkles and fine lines. This migration is often mentioned by women as being a major defect of conventional lipsticks and eyeshadows. The term "migration" is understood to mean running of the composition deposited on the lips or skin beyond its initial outline.

The gloss is essentially related to the nature of the liquid fatty phase. Thus, it is possible to reduce the level of waxes and fillers in the composition in order to increase the gloss of a lipstick, but then the migration of the liquid fatty phase increases. In other words, the levels of waxes and/or of fillers necessary for preparation of a stick of suitable hardness have been a restricting factor on the gloss of the deposit.

Document EP-A-1 068 856 describes wax-free solid cosmetic compositions, comprising a liquid fatty phase structured with a polymer, in which the fatty phase is primarily a non-silicone oil.

The use of fatty phases based on silicone oils nowadays makes it possible to obtain cosmetic compositions with long staying power when the oils are non-volatile or relatively non-volatile, namely good staying power over time of the colour (no colour change and no fading), and transfer-resistant compositions when the silicone oils are volatile, namely compositions that do not deposit onto a support such as a glass, a cup, a fabric or a cigarette, placed in contact with the film of makeup.

Currently, the use of silicone oils in cosmetics is limited by the small number of molecules, which are capable of gelling such oils to produce compositions in a solid form, such as cast lipsticks or foundations. The use of cosmetic compositions, whose fatty phase is predominantly silicone-based, leads to problems of compatibility with the ingredients, which are conventionally used in cosmetics.

In documents U.S. Pat. No. 5,874,069, U.S. Pat. No. 5,919,441, U.S. Pat. No. 6,051,216, WO-A-02/17870 and WO-A-02/17871, cosmetic compositions, such as deodorant gels or sticks, are prepared, comprising a silicone oily phase gelled with a wax based on polysiloxane and polyamide, or with a polymer comprising siloxane groups and groups capable of hydrogen interactions.

When these cosmetic compositions are used as deodorants, the problems of migration of the oily phase into wrinkles and fine lines, and the problems of the staying power and transfer resistance of the composition are not significant.

One aspect of the present invention is a care and/or makeup and/or treatment composition for the skin and/or the lips, which is able to overcome at least one of these drawbacks.

Surprisingly, the inventors have found that the use of specific polymers, in combination with specific solid particles makes it possible to structure, in the absence or presence of small amounts of wax, liquid fatty phases based on silicone oil, in the form of a makeup or care product whose application can produce a glossy or matt and migration-resistant film, and can reinforce the staying power and/or transfer-resistance properties of these products. Furthermore, their heat stability can be improved. As defined herein, "heat stability" means that the composition of the invention does not exude at room temperature for at least two months and up until nine months.

The present invention applies not only to makeup products for the lips, such as lipsticks, lip pencils and lip glosses, but also to care and/or treatment products for the skin, including the scalp, and for the lips, such as antisun stick products for the skin, the face or the lips, or lip balms, to makeup products for the skin, both of the human face and body, such as foundations cast in stick or dish form, concealer products and temporary tattoo products, to hygiene products and cleansing products, such as in stick form, and to makeup products for the eyes, such as eyeliners, in pencil form and mascaras, and cakes for keratin fibres (eyelashes, eyebrows or hair).

One aspect of the invention is a composition comprising a liquid fatty phase comprising at least one silicone oil, structured with a combination comprising:

1) at least one gelling agent chosen from homopolymers and copolymers with a weight-average molecular mass ranging from 500 to 500 000, comprising at least one moiety comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, carbamate (urethane), thiocarbamate, urea, thiourea, oxamido, guanidino and biguanidino groups, and combinations thereof on condition that at least one of the groups is other than an ester group, the at least one gelling agent being solid at room temperature and soluble in the liquid fatty phase at a temperature of from 25 to 250° C., and 2) solid particles having a hydrophobic surface, the liquid fatty phase, the at least one gelling agent, and the solid particles forming a physiologically acceptable medium.

As defined herein, "soluble in the liquid fatty phase" means that the polymer in the liquid fatty phase is observed to be a monophased product, i.e., a transparent single phase, at least at the softening point of the polymer.

As further defined herein, the term "polysiloxane" can be applied to a group comprising one organosiloxane unit and at least one other unit.

According to the invention, the composition may be in the form of a deformable or non-deformable solid.

According to the invention, the solid particles used in the compositions may be fillers or pigments. Generally, the mean size of the solid particles is from 10 nm to 50 μm, such as from 50 nm to 30 μm, and for example from 100 nm to 10 μm. Such particle sizes can readily be determined by one of ordinary skill in the art using known techniques.

The solid particles may be in the form of powders, fibres or platelets.

These fillers used in the cosmetic compositions generally can absorb sweat and sebum or provide a matt effect. According to the invention, these fillers furthermore can make it possible to structure the liquid fatty phase comprising a silicone oil and to reinforce the staying power and/or transfer-resistance properties of the composition, and also the heat stability.

According to the invention, in an anhydrous composition in stick form, such as lipsticks and concealer products in tube form, the fillers also make it possible to limit the exudation of the oil out of the tube even when the temperature is high, such as 45–47° C. and/or to limit the migration of the liquid fatty phase beyond its original application line, such as into wrinkles and fine lines.

The term "pigments" means any solid particle that is insoluble (as defined herein, "insoluble" means that one observes two phases and turbidity, i.e., cloudiness) in the composition and that serves to give and/or modify a colour and/or an iridescent appearance.

These pigments may be able to absorb sweat and sebum, and to colour or modify the appearance of the composition, such as the cosmetic makeup, treatment or body hygiene product. According to the invention, they also participate in structuring of the liquid fatty phase.

These fillers or pigments may be either hydrophobic or hydrophilic, on condition that they comprise, for example, a hydrophobic outer surface obtained, for example, by coating in a hydrophobic compound forming a hydrophobic film on their surface.

The hydrophobic pigments or fillers may comprise powders of crosslinked hydrophobic polymers or copolymers. Examples of crosslinked hydrophobic polymers and copolymers that may be mentioned include:
1°) fluoro polymers such as polytetrafluoroethylene powders and powders of a copolymer of tetrafluoroethylene and of olefin, for example of ethylene or of propylene;
2°) silicone elastomers, for example polymethylsilsesquioxane powders;
3°) polyolefins such as polyethylene;
4°) polyalkyl methacrylates, for example polymethyl methacrylate;
5°) polyamides;
6°) polystyrenes and derivatives, for example polymethylstyrene;
7°) polyesters;
8°) polyacrylics; and
9°) polyurethanes, for example hexamethylene diisocyanate (HDI)/trimethylol hexalactone powders.

Instead of powders, it is also possible to use fibres of hydrophobic nature, in particular fibres of the polymers and copolymers mentioned above, and also fillers in the form of platelets.

Other hydrophobic particles may comprise particles of lauroyllysine, and particles of pigments that block out ultraviolet rays.

Zinc oxides, titanium oxides or iron oxides whose elementary particle size is less than 1 μm, known as nanooxides or nanopigments, may also be used.

The solid particles may also comprise pigments and/or nacres for obtaining a covering makeup effect, that is to say, a makeup effect that does not allow the skin, the lips or integuments to show through. These particles also make it possible to reduce the sticky feel of the compositions.

The pigments may be white or coloured, mineral and/or organic, and coated or uncoated. Among the mineral pigments that may be mentioned are titanium dioxide, optionally surface-treated, zirconium oxide or cerium oxide, and also iron oxide, chromium oxide, manganese violet, ultramarine blue, chromium hydrate and ferric blue. Among the organic pigments that may be mentioned are carbon black, pigments of D & C type, and lakes based on cochineal carmine or on barium, strontium, calcium or aluminium. The pigments can be from 0% to 40%, such as from 1% to 35% and, further for example, from 2% to 25% of the total weight of the composition.

The nacreous pigments (or nacres) may be chosen from white nacreous pigments such as mica coated with titanium or with bismuth oxychloride, coloured nacreous pigments such as titanium mica with iron oxides, titanium mica with, for example, ferric blue or chromium oxide, titanium mica with an organic pigment of the above-mentioned type and also nacreous pigments based on bismuth oxychloride. They can be from 0% to 20% and, for example, from 0.1% to 15% of the total weight of the composition.

When the pigments or fillers are hydrophilic, for example pigments such as zinc oxides, iron oxides and titanium oxides, they are coated with a film of hydrophobic compound to introduce them into the liquid fatty phase of the composition of the invention, or they are subjected to a hydrophobic treatment.

The coating may comprise a surface treatment of the particles before introducing them into the fatty phase, for example, during their manufacture, or in situ.

The coating or surface treatment may be a fluoro coating such as a perfluoroalkyl monoester or diester of phosphoric acid (acid or salt), a perfluoropolyether, a perfluorocarboxylic or perfluorosulphonic acid, or a perfluoroalkyl diethanolamine phosphate salt.

The coating may be a coating or a grafting based on fluorosilicone, for example a grafting with a silane comprising a perfluoroalkyl group.

The surface treatment may also be carried out using silicone derivatives, for example grafting with reactive silicones initially comprising hydrogenosilane groups, grafting with a diorganosilane such as dimethylchlorosilane or with an alkylalkoxysilane, grafting with a silane comprising a glycidoxypropyl group, coating with a polyglycerolated silicone, or coating with a silicone-grafted acrylic copolymer or silicone-grafted-polyacrylic.

A coating with N-acylamino acids, for example N-lauroyllysine, coatings with fatty acids or fatty acid salts of the stearic acid type, coatings with lecithins and coatings with ester oils may also be used.

In the composition of the invention, the amount of polymer acting as gelling agent generally is, for example, from 0.5% to 80% relative to the total weight of the composition, further for example from 2% to 60% and still further for example from 5% to 40%, the amount of solid particles with a hydrophobic surface may be, for example, from 0.1% to 90% of the total weight of the composition, further for example from 1% to 70% and still further for example from 2% to 50%, and even further for example from 5% to 25% of the total weight of the composition.

Moreover, the gelling polymer/silicone oil(s) ratio by mass is for example from 0.1% to 50%.

The liquid fatty phase for example comprises at least 40% and further for example at least 50% by weight of at least one silicone oil, having a viscosity, for example, of less than 5 000 cSt and for example less than 3 000 cSt, since the silicone polymers used in the invention are more soluble in silicone oils of low viscosity. It may also comprise other non-silicone oils or mixture of oils.

The silicone oils that may be used in the invention may be volatile or non-volatile, linear or cyclic polydimethylsiloxanes (PDMSs), that are liquid at room temperature; polydimethylsiloxanes comprising alkyl, alkoxy or phenyl groups, that are pendent and/or at the end of a silicone chain, the groups each comprising from 2 to 24 carbon atoms; phenylsilicones, for instance phenyl trimethicones, phenyl dimethicones, phenyl trimethylsiloxydiphenylsiloxanes, diphenyl dimethicones, diphenyl methyldiphenyl trisiloxanes and 2-phenylethyl trimethylsiloxysilicates.

The liquid fatty phase may also comprise other non-silicone oils, for example polar oils such as:

hydrocarbon-based plant oils with a high triglyceride content comprising fatty acid esters of glycerol, the fatty acids of which may have varied chain lengths, these chains possibly being linear or branched, and saturated or unsaturated; these oils are especially wheatgerm oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grapeseed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearines Dubois or those sold under the names Miglyol 810, 812 and 818 by the company Dynamit Nobel;

synthetic oils or esters of formula $R_5COOR_6$ in which $R_5$ is chosen from linear and branched higher fatty acid residues comprising from 1 to 40 and for example from 7 to 19 carbon atoms, and $R_6$ is chosen from linear and branched hydrocarbon-based chains comprising from 1 to 40 and for example from 3 to 20 carbon atoms, with $R_5+R_6 \geq 10$, such as, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for example isostearyl lactate or diisostearyl malate; and pentaerythritol esters;

synthetic ethers comprising from 10 to 40 carbon atoms; $C_8$ to $C_{26}$ fatty alcohols, for example oleyl alcohol; and mixtures thereof.

The liquid fatty phase may also comprise apolar oils such as linear and branched hydrocarbons and fluorocarbons of synthetic and mineral origins, which may be volatile and non-volatile, for instance volatile liquid paraffins (such as isoparaffins or isododecane) and non-volatile liquid paraffins and derivatives thereof, petroleum jelly, polydecenes, hydrogenated polyisobutene such as parleam and squalane, and mixtures thereof.

Generally, the liquid fatty phase represents, for example, from 5% to 99% of the total weight of the composition and further for example from 20% to 75%.

The polymers used as gelling agents in the composition of the invention are polymers of the polyorganosiloxane type such as those described in documents U.S. Pat. Nos. 5,874, 069, 5,919,441, 6,051,216 and 5,981,680.

According to the invention, the polymers used as gelling agent may, for example, belong to the following two families:

1) polyorganosiloxanes comprising at least two groups capable of establishing hydrogen interactions, these two groups being located in the polymer chain; and/or
2) polyorganosiloxanes comprising at least two groups capable of establishing hydrogen interactions, these two groups being located on grafts or branches.

According to the invention, the polymers can be solids that may be dissolved beforehand in a solvent with hydrogen interaction capable of breaking the hydrogen interactions of the polymers, for instance $C_2$ to $C_8$ lower alcohols, such as ethanol, n-propanol and isopropanol, before being placed in the presence of the silicone oils according to the invention. It is also possible to use these hydrogen interaction "breaking" solvents as co-solvents. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

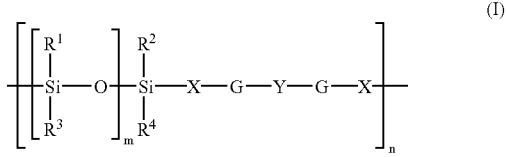

(I)

in which:
1) $R^1$, $R^2$, $R^3$ and $R^4$, which may be identical or different, are chosen from:
   linear, branched and cyclic, saturated and unsaturated, $C_1$ to $C_{40}$ hydrocarbon-based groups, optionally comprising in their chain at least one atom selected from oxygen, sulphur and nitrogen, and may also optionally be partially or totally substituted with at least one fluorine atom,
   $C_6$ to $C_{10}$ aryl groups, optionally substituted with at least one $C_1$ to $C_4$ alkyl group,
   polyorganosiloxane chains optionally comprising at least one atom chosen from oxygen, sulphur and nitrogen;
2) the groups X, which may be identical or different, are chosen from linear and branched $C_1$ to $C_{30}$ alkylenediyl groups, optionally comprising at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by at least one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl, and $C_1$ to $C_6$ aminoalkyl, or 4) Y represents a group corresponding to the formula:

in which
T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and $R^5$ is chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

5) the groups G, which may be identical or different, represent divalent groups chosen from:

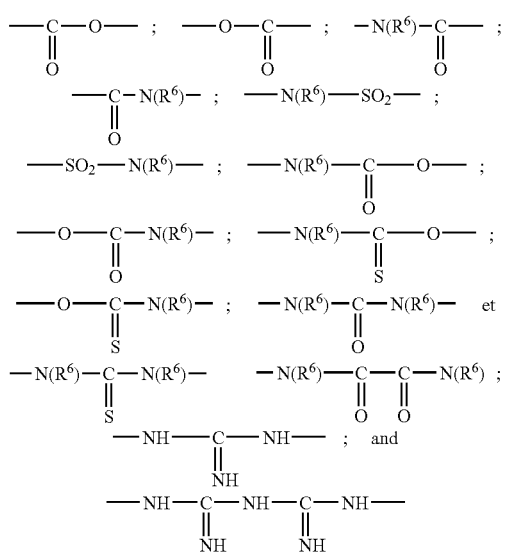

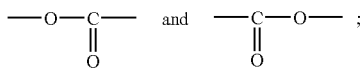

in which $R^6$ is chosen from a hydrogen atom and linear and branched $C_1$ to $C_{20}$ alkyl groups, on condition that at least 50% of the groups $R^6$ of the polymer represent a hydrogen atom and that at least two of the groups G of the polymer are a group other than:

—O—C(=O)—   and   —C(=O)—O— ;

6) n is an integer ranging from 2 to 500 and for example, from 2 to 200, and m is an integer ranging from 1 to 1 000, for example from 1 to 700 and further for example from 6 to 200.

According to the invention, 80% of the groups $R^1$, $R^2$, $R^3$ and $R^4$ of the polymer are for example chosen from methyl, ethyl, phenyl and 3,3,3-trifluoropropyl groups.

According to the invention, Y can also represent various divalent groups, furthermore optionally comprising one or two free valencies to establish bonds with other moieties of the polymer or copolymer. For example, Y represents a group chosen from:

a) linear $C_1$ to $C_{20}$ and for example $C_1$ to $C_{10}$ alkylene groups,
b) $C_{30}$ to $C_{56}$ branched alkylene groups optionally comprising rings and unconjugated unsaturations,
c) $C_5$–$C_6$ cycloalkylene groups,
d) phenylene groups optionally substituted with at least one $C_1$ to $C_{40}$ alkyl group,
e) $C_1$ to $C_{20}$ alkylene groups comprising from 1 to 5 amide groups,
f) $C_1$ to $C_{20}$ alkylene groups comprising at least one substituent chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

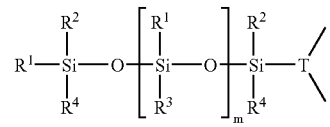

in which $R^1$, $R^2$, $R^3$, $R^4$, T and m are as defined above, and
h) polyorganosiloxane chains of formula:

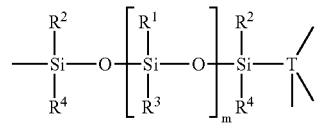

in which $R^1$, $R^2$, $R^3$, $R^4$, T and m are as defined above.

The polyorganosiloxanes of the second family may be polymers comprising at least one moiety corresponding to formula (II):

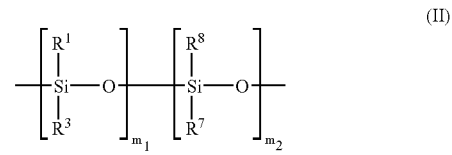

in which
$R^1$ and $R^3$, which may be identical or different, are as defined above for formula (I),
$R^7$ is chosen from a group as defined above for $R^1$ and $R^3$, and a group of formula —X-G-$R^9$ in which X and G are as defined above for formula (1) and $R^9$ is chosen from a hydrogen atom and linear, branched and cyclic, saturated and unsaturated, $C_1$ to $C_{50}$ hydrocarbon-based groups optionally comprising in the chain at least one atom chosen from O, S and N, optionally substituted with at least one fluorine atom and/or at least one hydroxyl group, and a phenyl group optionally substituted with at least one $C_1$ to $C_4$ alkyl group,
$R^8$ represents a group of formula —X-G-$R^9$ in which X, G and $R^9$ are as defined above,
$m_1$ is an integer ranging from 1 to 998, and
$m_2$ is an integer ranging from 2 to 500.

According to the invention, the polymer used as gelling agent may be a homopolymer, that is to say a polymer comprising several identical moieties, in particular moieties of formula (I) or of formula (II) above.

According to the invention, it is also possible to use a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also optional to use a copolymer comprising at least one moiety of formula (I) and at least one moiety of formula (II), the moieties of formula (I) and the moieties of formula (II) optionally being identical to or different from each other.

According to one variant of the invention, it is also optional to use a copolymer furthermore comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to a first embodiment of the invention, the groups capable of establishing hydrogen interactions are amide groups of formulae —C(O)NH— and —HN—C(O)—.

In this case, the gelling agent may be a polymer comprising at least one moiety chosen from formulae (III) and (IV):

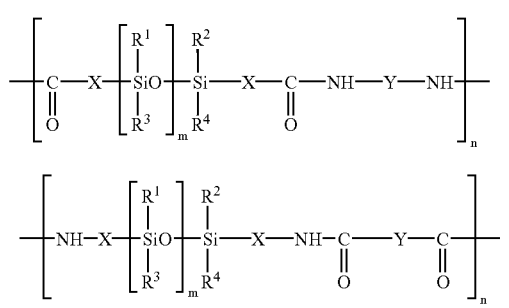

(III)

and (IV)

in which $R^1$, $R^2$, $R^3$, $R^4$, X, Y, m and n are as defined above.

Such a moiety may be obtained:

either by a condensation reaction between a silicone comprising α,ω-carboxylic acid ends and at least one diamine, according to the following reaction scheme:

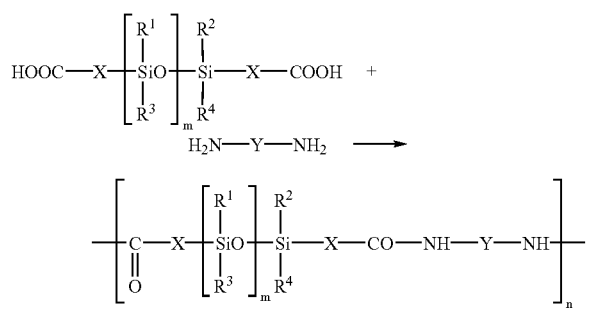

in which $R^1$, $R^2$, $R^3$, $R^4$, X, Y, m and n are as defined above.

or by reaction of two molecules of α-unsaturated carboxylic acid with a diamine according to the following reaction scheme:

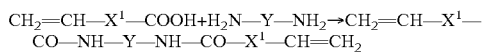

$$CH_2=CH-X^1-COOH+H_2N-Y-NH_2 \rightarrow CH_2=CH-X^1-CO-NH-Y-NH-CO-X^1-CH=CH_2$$

followed by the addition of a siloxane to the ethylenic unsaturations, according to the following scheme:

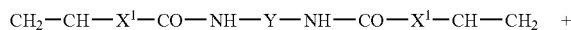

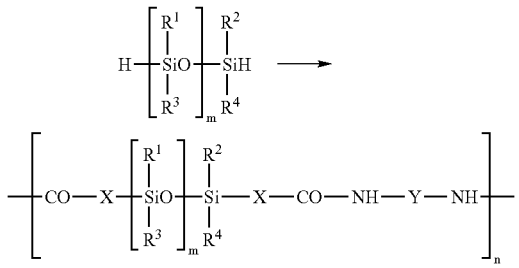

in which $X^1$—$(CH_2)_2$— corresponds to X defined above and Y, $R^1$, $R^2$, $R^3$, $R^4$ and m are as defined above;

or by reaction of a silicone comprising α,ω-$NH_2$ ends and a diacid of formula HOOC—Y—COOH according to the following reaction scheme:

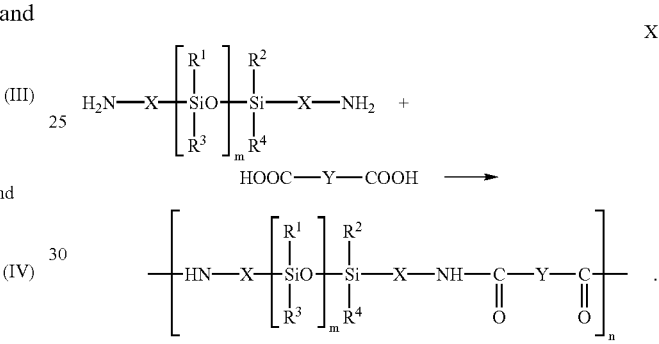

In these polyamides of formulae (III) and (IV), m is for example in the range from 1 to 700, further for example from 15 to 500 and further for example from 15 to 45, and n is for example in the range from 1 to 500, further for example from 1 to 100 and further for example from 4 to 25, X, is for example chosen from linear and branched alkylene chains comprising from 1 to 30 carbon atoms and for example 3 to 10 carbon atoms, and Y is for example chosen from alkylene chains that are linear and branched and that optionally comprise rings and/or unsaturations, comprising from 1 to 40 carbon atoms, for example from 1 to 20 carbon atoms and further for example from 2 to 6 carbon atoms, and even further for example 6 carbon atoms.

In formulae (III) and (IV), the alkylene group representing X or Y can optionally comprise in its alkylene portion at least one of the following elements:

1°) 1 to 5 amide, urea or carbamate groups,

2°) a $C_5$ or $C_6$ cycloalkyl group, and

3°) a phenylene group optionally substituted with 1 to 3 identical or different $C_1$ to $C_3$ alkyl groups.

In formulae (III) and (IV), the alkylene groups may also be substituted with at least one element chosen from:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and
a $C_1$ to $C_6$ aminoalkyl group.

In these formulae (III) and (IV), Y may also represent:

in which $R^5$ represents a polyorganosiloxane chain and T represents a group of formula:

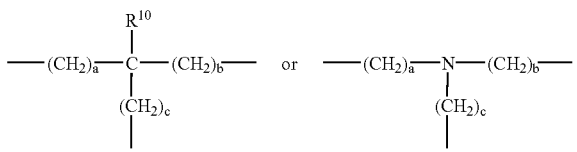

in which a, b and c are, independently, integers ranging from 1 to 10, and $R^{10}$ is chosen from a hydrogen atom and a group such as those defined for $R^1$, $R^2$, $R^3$ and $R^4$ above.

In formulae (III) and (IV), $R^1$, $R^2$, $R^3$ and $R^4$ for example, are chosen from, independently, linear and branched $C_1$ to $C_{40}$ alkyl groups, for example $CH_3$, $C_2H_5$, n-$C_3H_7$ and isopropyl groups, a polyorganosiloxane chain and a phenyl group optionally substituted with one to three methyl or ethyl groups.

As has been seen previously, the polymer may comprise identical or different moieties chosen from formulae (III) and (IV).

Thus, the polymer may be a polyamide comprising several moieties chosen from formulae (III) and (IV) of different lengths, i.e. a polyamide corresponding to the formula:

(V)

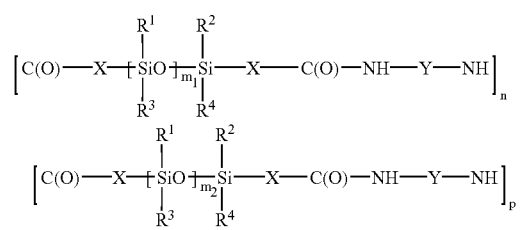

in which X, Y, n and $R^1$ to $R^4$ have the meanings given above, $m_1$ and $m_2$, which are different, are integers chosen in the range from 1 to 1 000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example comprising different groups Y. In this case, the copolymer may correspond to the formula:

(VI)

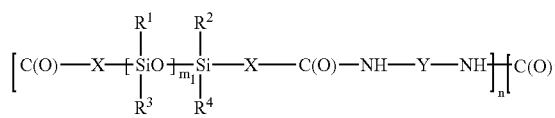

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In this first embodiment of the invention, the gelling agent may also comprise a grafted copolymer. Thus, the polyamide comprising silicone units may be grafted and optionally crosslinked with silicone chains comprising amide groups. Such polymers may be synthesized with trifunctional amines.

In this case, the copolymer may comprise at least one moiety of formula:

(VII)

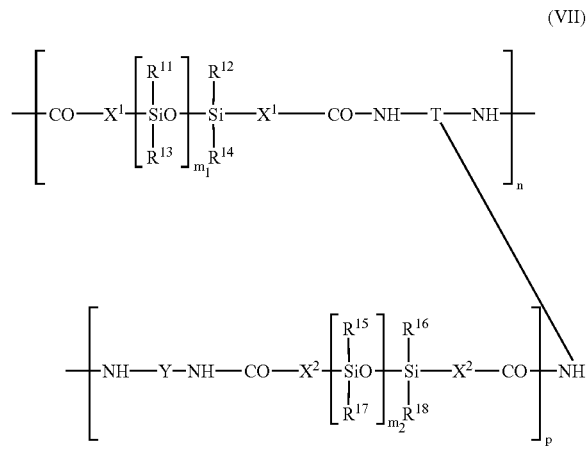

in which $X^1$ and $X^2$, which may be identical or different, have the meaning given for X in formula (I), n is as defined in formula (I), Y and T are as defined in formula (I), $R^{11}$ to $R^{18}$ are groups chosen from the same groups as $R^1$ to $R^4$, $m_1$ and $m_2$ are integers in the range from 1 to 1 000, and p is an integer ranging from 2 to 500.

In formula (VII), for example:
p is in the range from 1 to 25 and further for example from 1 to 7,
$R^{11}$ to $R^{18}$ are methyl groups,
T corresponds to one of the following formulae:

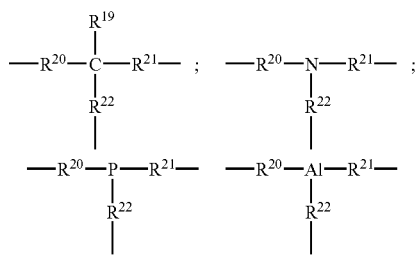

in which $R^{19}$ is chosen from a hydrogen atom and a group chosen from the groups defined for $R^1$ to $R^4$ above, and $R^{20}$, $R^{21}$ and $R^{22}$ are, independently, chosen from linear and branched alkylene groups, and for example T corresponds to the formula:

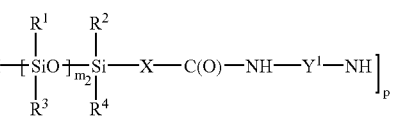

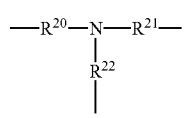

wherein, for example, $R^{20}$, $R^{21}$ and $R^{22}$ represent —$CH_2$—$CH_2$—, $m_1$ and $m_2$ are in the range from 15 to 500 and further for example from 15 to 45, $X^1$ and $X^2$ represent —$(CH_2)_{10}$—, and Y represents —$CH_2$—.

These polyamides comprising a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight of the total weight of the copolymer.

According to the invention, as has been seen previously, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, for example, the siloxane-based polyamides are:

polyamides of formula (III) in which m is from 15 to 50;

mixtures of at least two polyamides in which at least one polyamide has a value of m in the range from 15 to 50 and at least one polyamide has a value of m in the range from 30 to 50;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;

mixtures of polyamide of formula (III) combining 1) 80% to 99% by weight of a polyamide in which n is equal to 2 to 10 and for example 3 to 6, and 2) 1% to 20% of a polyamide in which n is in the range from 5 to 500 and for example from 6 to 100;

polyamides corresponding to formula (VI) in which at least one of the groups Y and $Y^1$ comprises at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$—; and polyamides of formula (III) in which the polyamides end with a monofunctional chain chosen from monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is α,ω-diaminated, or a monoamine if the silicone is an α,ω-dicarboxylic acid.

According to one embodiment variant of the invention, it is possible to use a copolymer of silicone polyamide and of hydrocarbon-based polyamide, i.e. a copolymer comprising moieties chosen from formulae (III) and (IV) and hydrocarbon-based polyamide moieties. In this case, the polyamide-silicone moieties may be arranged at the ends of the hydrocarbon-based polyamide.

Polyamide-based gelling agents comprising silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide comprising free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, for example 2 to 50 and further for example 2, 6, 9.5, 12, 13.5, 23 or 31 siloxane groups, may be used for the reaction with hydrocarbon-based polyamides based on fatty acid dimers. Siloxane diamines comprising 13.5 siloxane groups are preferred, and the best results are obtained with the siloxane diamine comprising 13.5 siloxane groups and polyamides comprising high numbers of carboxylic acid end groups (for example polyamides comprising high acid numbers, for example from 15 to 20).

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide comprising free amine groups, by amidation reaction with a siloxane comprising an acid group.

It is also possible to prepare a gelling agent based on a copolymer between a hydrocarbon-based polyamide and a silicone polyamide, by transamidation of a polyamide having, for example, an ethylene-diamine constituent, with an oligosiloxane-α,ω-diamine, at a high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to a second embodiment of the invention, the gelling agent is chosen from homopolymers and copolymers comprising at least one group chosen from urethanes and urea groups.

As previously, the gelling agent may comprise at least one polyorganosiloxane moiety comprising at least two groups chosen from urethane and urea groups, either in the backbone of the polymer or on side chains or as pendent groups.

The gelling agent comprising at least two groups chosen from urethane and urea groups in the backbone may be chosen from polymers comprising at least one moiety corresponding to the following formula:

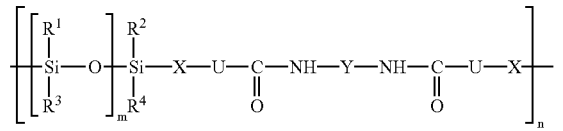

(VIII)

in which $R^1$, $R^2$, $R^3$, $R^4$, X, Y, m and n have the meanings given above for formula (I), and U represents —O— or —NH—, such that:

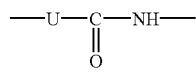

corresponds to a urethane or urea group.

In this formula (VIII), Y, may be chosen from linear and branched $C_1$ to $C_{40}$ alkylene groups, optionally substituted with a group chosen from $C_1$ to $C_{15}$ alkyl groups and $C_5$ to $C_{10}$ aryl groups. For example, a —$(CH_2)_6$— group is used.

Y may also be a group chosen from $C_5$ to $C_{12}$ cycloaliphatic and aromatic groups that may be substituted with a group chosen from $C_1$ to $C_{15}$ alkyl groups and $C_5$ to $C_{10}$ aryl groups, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Y may be chosen from linear and branched $C_1$ to $C_{40}$ alkylene radicals and $C_4$ to $C_{12}$ cycloalkylene radicals.

Y may also be chosen from polyurethane and polyurea blocks corresponding to the condensation of several diisocyanate molecules with at least one molecule of coupling agents of the diol and diamine types. In this case, Y comprises several urethane or urea groups in the alkylene chain.

Y may correspond to the formula:

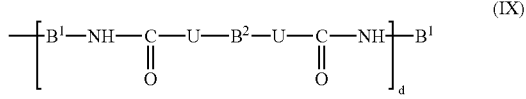

(IX)

in which $B^1$ is a group chosen from the groups given above for Y, U is —O— or —NH— and $B^2$ is chosen from:

linear and branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

in which T is a hydrocarbon-based trivalent radical optionally comprising at least one hetero atom such as oxygen, sulphur and nitrogen and $R^5$ is chosen from polyorganosiloxane chains and linear and branched $C_1$ to $C_{50}$ alkyl chains.

T can be chosen from, for example:

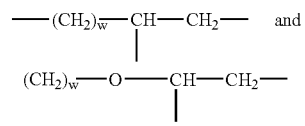

with w being an integer ranging from 1 to 10 and $R^5$ being a polyorganosiloxane chain.

Y can be chosen from linear and branched $C_1$ to $C_{40}$ alkylene groups, for example, the —$(CH_2)_2$— and —$(CH_2)_6$— groups.

In the formula given above for Y, d may be an integer ranging from 0 to 5, for example from 0 to 3 and further for example equal to 1 or 2.

For example, $B^2$ is chosen from linear and branched $C_1$ to $C_{40}$ alkylene groups, such as —$(CH_2)_2$— and —$(CH_2)_6$— groups and groups of:

with $R^5$ being a polyorganosiloxane chain.

As previously, the polymer constituting the gelling agent may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

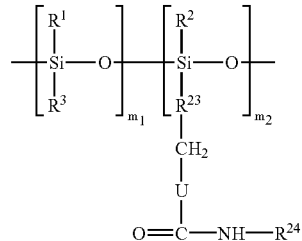

(X)

in which $R^1$, $R^2$, $R^3$, $m_1$ and $m_2$ have the meanings given above for formula (I), U is chosen from O and NH, $R^{23}$ is chosen from $C_1$ to $C_{40}$ alkylene groups, optionally comprising at least one hetero atom chosen from O and N, and a phenylene group, and $R^{24}$ is chosen from linear, branched and cyclic, saturated and unsaturated $C_1$ to $C_{50}$ alkyl groups, and phenyl groups optionally substituted with one to three $C_1$ to $C_3$ alkyl groups.

The polymers comprising at least one moiety of formula (X) comprise at least one siloxane unit and at least one urea or urethane group, and they may be used as gelling agents in the compositions of the invention.

The siloxane polymers may comprise a single urea or urethane group by branching or may comprise branches comprising two urea or urethane groups, or may comprise a mixture of branches comprising one urea or urethane group and branches comprising two urea or urethane groups.

The siloxane polymers may be obtained from branched polysiloxanes, comprising one or two amino groups by branching, by reacting these polysiloxanes with monoisocyanates.

As examples of starting polymers of this type comprising amino and diamino branches, mention may be made of the polymers corresponding to the following formulae:

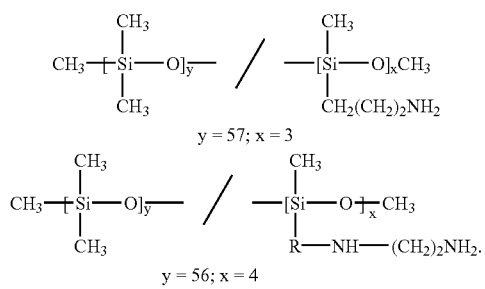

In these formulae, the symbol "/" indicates that the segments may be of different lengths and in a random order, and R represents a linear aliphatic group for example comprising 1 to 6 carbon atoms and further for example 1 to 3 carbon atoms.

Such polymers comprising branching may be formed by reacting a siloxane polymer, comprising at least three amino groups per polymer molecule, with a compound comprising only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer comprising at least one siloxane unit and at least one group capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at a high temperature, the temperature of the system then being reduced to form the gel.

Exemplary polymers that can be incorporated into the compositions according to the present invention are, for example, siloxane-urea copolymers that are linear and that comprise urea groups as the groups capable of establishing hydrogen interactions in the backbone of the polymer.

As an illustration of a polysiloxane ending with four urea groups, mention may be made of the polymer of formula:

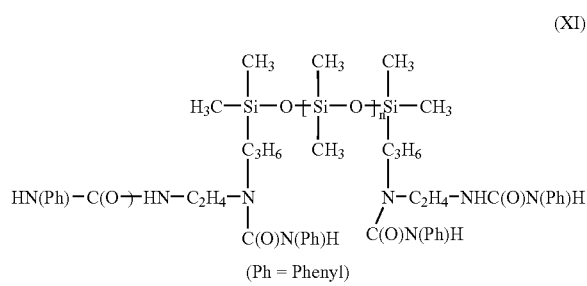

in which Ph is a phenyl group and n is a number from 0 to 300, for example from 0 to 100, and further for example 50.

This polymer is obtained by reacting the following polysiloxane comprising amino groups:

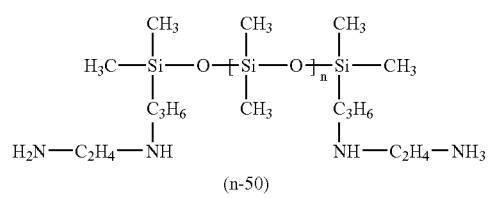

with phenyl isocyanate.

The polymers of formula (VIII) comprising at least one urea or urethane group in the chain of the silicone polymer may be obtained by reaction between a silicone comprising $\alpha,\omega$-$NH_2$ or —OH end groups, of formula:

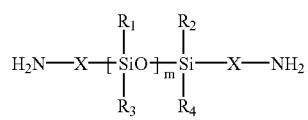

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may correspond to the formula (IX) with d equal to 0 or d equal to 1 to 5.

As in the case of the polyamide silicones of formula (II) or (III), it is possible to use in the invention at least one polyurethane or polyurea silicone comprising moieties of different length and structure, for example moieties whose lengths differ by the number of silicone units. In this case, the copolymer may correspond, for example, to the formula:

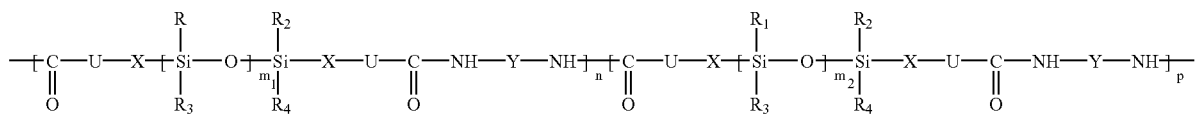

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

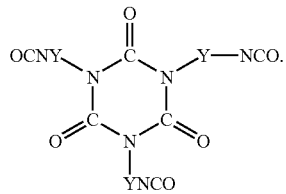

A polyurethane or polyurea silicone comprising branches comprising an organosiloxane chain with groups capable of establishing hydrogen interactions is thus obtained. Such a polymer comprises, for example, a moiety corresponding to the formula:

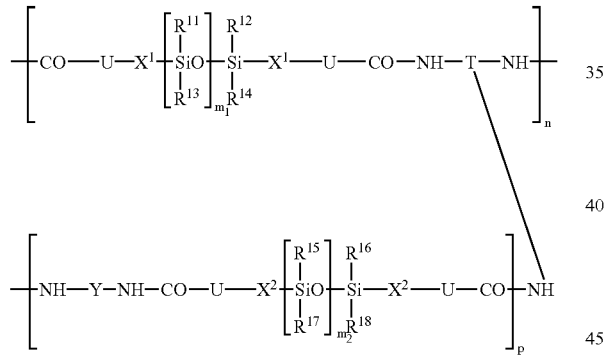

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$ in formula (I), $m_1$ and $m_2$ are integers in the range from 1 to 1 000, and p is an integer ranging from 2 to 500.

As in the case of the polyamides, this copolymer can also comprise at least one polyurethane silicone moiety without branching.

In this second embodiment of the invention, the siloxane-based polyureas and polyurethanes are, for example:

polymers of formula (VII) in which m is from 15 to 50;

mixtures of at least two polymers in which at least one polymer has a value of m in the range from 15 to 50 and at least one polymer has a value of m in the range from 30 to 50;

polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining
1) 80% to 99% by weight of a polymer in which n is equal to 2 to 10 and for example 3 to 6, and
2) 1% to 20% of a polymer in which n is in the range from 5 to 500 and for example from 6 to 100, copolymers comprising two moieties of formula (VIII) in which at least one of the groups Y comprises at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group comprising monofunctional amines, monofunctional acids, monofunctional alcohols, including fatty acids, fatty alcohols and fatty amines, such as, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, gelling agents comprising homopolymers or copolymers of the invention may comprise at least one siloxane moiety in the main chain of the polymer and at least one group capable of establishing hydrogen interactions, either in the main chain of the polymer or at the ends thereof, or on side chains or branches of the main chain. This may correspond to the following five arrangements:

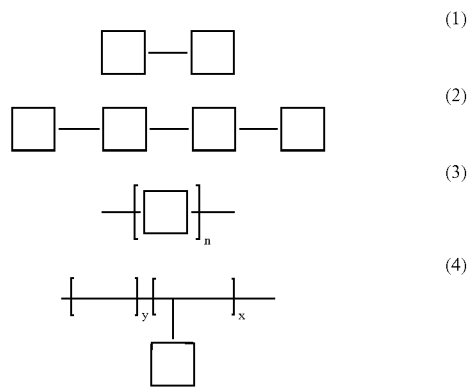

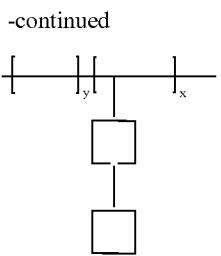

in which the continuous line is the main chain of the siloxane polymer and the squares represent the groups capable of establishing hydrogen interactions.

In case (1), the groups capable of establishing hydrogen interactions are arranged at the ends of the main chain. In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

According to the invention, the structuring of the liquid fatty phase comprising at least one silicone oil is obtained with the aid of at least one of the polymers mentioned above, in combination with solid particles having a hydrophobic surface.

As examples of polymers that may be used, mention may be made of the silicone polyamides obtained in accordance with Examples 1 and 2 of document U.S. Pat. No. 5,981,680.

The polymers and copolymers used as gelling agents in the composition of the invention may have a softening point from 40 to 190° C. For example, they have a softening point ranging from 50 to 140° C. and further for example from 70° C. to 120° C. This softening point is lower than that of the known structuring polymers, which facilitates the use of the polymers that are the subject of the invention, and limits the deteriorations of the liquid fatty phase.

They have good solubility in the silicone oils and produce macroscopically homogeneous compositions. For example, they have an average molecular mass from 500 to 200 000, further for example from 1 000 to 100 000 and even further for example from 2 000 to 30 000.

According to the invention, the composition, for example, has a hardness ranging from 20 to 2 000 gf and further for example from 20 to 900 gf, further for example from 20 to 600 gf, and even further for example from 150 to 450 gf. This hardness may be measured according to a method of penetration of a probe into the said composition and, for example, with the aid of a texture analyser (for example TA-TXT2, from Rheo) equipped with an ebonite cylinder 25 mm in height and 8 mm in diameter. The hardness measurement is carried out at 20° C. at the centre of five samples of the said composition. The cylinder is introduced into each sample of composition at a pre-speed of 2 mm/s, then at a speed of 0.5 mm/s and finally at a post-speed of 2 mm/s, the total displacement being 1 mm. The recorded hardness value is that of the maximum peak. The measurement error is ±50 gf.

The hardness may also be measured by the "cheese wire" method, which involves cutting a tube of lipstick 8.1 mm in diameter and measuring the hardness at 20° C., using a DFGHS 2 tensile testing machine from the company Indelco-Chatillon, travelling at a speed of 100 mm/minute. It is expressed as the shear force (expressed in grams-force) required to cut a stick under these conditions. According to this method, the hardness of a composition in stick form according to the invention ranges from 30 to 300 gf, for example from 30 to 200 gf, and further for example from 30 to 120 gf.

The hardness of the composition according to the invention can be such that the composition is self-supporting and can be disintegrated easily to form a satisfactory deposit on the skin and the lips. In addition, with this hardness, the composition of the invention shows good impact strength.

According to the invention, the composition in stick form has the behaviour of a deformable and supple elastic solid, giving noteworthy elastic softness on application. The stick compositions of the prior art do not have this property of elasticity and suppleness.

The polymer content is chosen according to the desired gel hardness and as a function of the particular application intended. The amount of polymer should be such that it allows a disintegrable stick to be obtained. In practice, the amount of polymer (as active material) represents, for example, from 0.5% to 80% of the total weight of the composition, further for example from 2% to 60% and even further for example from 5% to 40%.

The composition of the invention may also comprise any ingredient usually used in the field under consideration, and especially those chosen from dyes that are soluble in polyols or in the fatty phase, water mentioned in antioxidants, essential oils, preserving agents, fragrances, liposoluble polymers, especially hydrocarbon-based liposoluble polymers such as polyalkylenes or polyvinyl laurate, liquid-fatty-phase gelling agents, waxes, gums, resins, surfactants, for instance trioleyl phosphate, additional cosmetic or dermatological active agents such as, for example, water, emollients, moisturizers, vitamins, liquid lanolin, essential fatty acids, lipophilic sunscreens or sunscreens that are soluble in polyols, and mixtures thereof. The composition according to the invention may also comprise lipid vesicles of ionic and/or nonionic type. These ingredients, besides the water, may be present in the composition in the usual manner in a proportion of from 0% to 20% of the total weight of the composition and for example from 0.1% to 10%.

Needless to say, the person skilled in the art will take care to select the optional additional ingredients and/or the amount thereof such that all advantageous properties of the composition according to the invention are not, or are not substantially, adversely affected by the envisaged addition.

In the case where the composition comprises an aqueous phase, which is the case for a water-in-oil or oil-in-water simple emulsion or a water-in-oil-in-water or oil-in-water-in-oil multiple emulsion, this aqueous phase can represent 0.1% to 70% by weight of the composition, for example from 0.5% to 40% and further for example from 1% to 20%. This aqueous phase can comprise water and any water-miscible compound, for instance polyols. This aqueous phase may also be gelled with suitable gelling agents. For example, the composition of the invention is in the form of a continuous fatty phase and further for example in anhydrous form.

The composition of the invention may for example comprise at least one wax, for example polyethylene wax, but the use of wax is avoided if it is desired to obtain glossy products. Generally, the amount of wax does not exceed 20% and in one example, 10% of the total weight of the composition. It represents, for example, from 3% to 5% of the total weight of the composition.

The composition of the invention may also comprise dispersants.

The composition according to the invention may be in the form of an optionally tinted dermatological or care composition for keratin materials such as the skin, the lips and/or integuments, in the form of an antisun protective composition or body hygiene composition, for example, in the form of a makeup-removing product in stick form. It can also be used as a care base for the skin, integuments or the lips (lip balms, for protecting the lips against the cold and/or sunlight and/or the wind, or a care cream for the skin, the nails or the hair).

The composition of the invention may also be in the form of a coloured makeup product for the skin, such as a foundation, optionally having care or treatment properties, a blusher, a face powder, an eyeshadow, a concealer product, an eyeliner or a makeup product for the body; a lip makeup, for instance a lipstick, optionally having care or treatment properties; a makeup for integuments, for instance the nails or the eyelashes, such as in the form of a mascara cake, or for the eyebrows and the hair, such as in the form of a pencil. Further for example, the composition of the invention may be a cosmetic product comprising cosmetic and/or dermatological active agents, for instance moisturizers, ceramides, vitamins, sunscreens or cicatrizing agents.

In the case of makeup compositions, hydrophobic solid particles may constitute the pigment(s) for making up the skin, the lips and/or integuments.

Needless to say, for cosmetic and dermatological uses, the composition of the invention must be cosmetically or dermatologically acceptable, that is to say that it must comprise a non-toxic physiologically acceptable medium that can be applied to the skin, integuments or the lips of human beings. For the purposes of the invention, the term "cosmetically acceptable" is understood to mean a composition of at least one of pleasant appearance, odour, feel and possibly taste.

According to the invention, the composition may also be in the form of a transparent anhydrous rigid gel in the absence of diffusing particles, for instance certain fillers and pigments, such as in the form of a transparent anhydrous stick.

According to the invention, the composition may furthermore comprise a dyestuff that may be chosen from lipophilic dyes and hydrophilic dyes, and mixtures thereof.

The liposoluble dyes are, for example, Sudan red, DC Red 17, DC Green 6, β-carotene, soybean oil, Sudan brown, DC Yellow 11, DC Violet 2, DC Orange 5, quinoline yellow and annatto. They can represent from 0% to 20% of the weight of the composition and for example from 0.1% to 6%.

The composition according to the invention may be manufactured by the known processes, generally used in cosmetics or dermatology. It may be manufactured by the process that comprises heating the polymer at least to its softening point, adding the oil(s) thereto, the particles, if necessary the dyestuffs and the additives, and then mixing the whole until a solution that is homogeneous to the naked eye is obtained. The homogeneous mixture obtained can then be cast in a suitable mould, for instance a lipstick mould, or directly into the packaging articles (especially a case or dish).

Another aspect of the invention is a cosmetic care, makeup or treatment process for a human keratin material and for example the skin, the lips and integuments, comprising the application to the keratin material of the composition, I.e., the cosmetic composition, as defined above.

Another aspect of the invention is a method of structuring a composition in the form of a self-supporting solid with a hardness ranging from 20 to 2 000 gf and for example from 20 to 900 gf and further for example from 20 to 600 gf, comprising including in said composition a liquid continuous fatty phase comprising at least one silicone oil, structured with a sufficient amount of at least one polymer chosen from homopolymers and copolymers with a weight-average molecular mass ranging from 500 to 500 000, and for example from 2 000 to 30 000, comprising at least one moiety comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group, the at least one polymer being solid at room temperature and soluble in the liquid fatty phase at a temperature of from 25 to 250° C., and solid particles having a hydrophobic surface.

Another aspect of the invention is a method of manufacturing a physiologically acceptable, rigid, self-supporting, glossy and/or migration-resistant composition, comprising including in said composition a continuous liquid fatty phase comprising at least one silicone oil, structured with a sufficient amount of at least one polymer chosen from homopolymers and copolymers with a weight-average molecular mass ranging from 500 to 500 000, comprising at least one moiety comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group, the at least one polymer being solid at room temperature and soluble in the liquid fatty phase at a temperature of from 25 to 250° C., and solid particles having a hydrophobic surface.

Another aspect of the invention is a method of structuring a composition in the form of a self-supporting solid, comprising including in said composition a liquid continuous fatty phase comprising at least one silicone oil, structured with a sufficient amount of at least one polymer chosen from homopolymers and copolymers with a weight-average molecular mass of from 500 to 500 000, comprising at least one moiety comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group, the at least one polymer being solid at room temperature and soluble in the liquid fatty phase at a temperature of from 25 to 250° C., and solid particles having a hydrophobic surface.

Another aspect of the invention is an agent in a cosmetic composition or a physiologically acceptable composition for limiting the migration of the said composition, wherein the agent comprises a continuous liquid fatty phase, comprising at least one silicone oil, structured with a sufficient amount of at least one polymer chosen from homopolymers and copolymers with a weight-average molecular mass ranging from 500 to 500 000, comprising at least one moiety comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group, the at least one polymer being solid at room temperature and soluble in the liquid fatty phase at a temperature of from 25 to 250° C., and solid particles having a hydrophobic surface.

Another aspect of the invention is a cosmetic process for limiting the migration of a cosmetic composition or manufacturing a physiologically acceptable composition comprising including in the cosmetic or physiologically acceptable composition an anti-migration agent comprising a liquid fatty phase comprising at least one silicone oil, structured with a sufficient amount of at least one polymer chosen from homopolymers and copolymers with a weight-average molecular mass ranging from 500 to 500 000, comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group, the at least one polymer being solid at room temperature and soluble in the liquid fatty phase at a temperature of from 25 to 250° C., and solid particles having a hydrophobic surface.

Another aspect of the invention is a makeup stick for the skin, the lips and/or integuments, and for example for the lips, comprising solid particles having a hydrophobic surface comprising at least one pigment in an amount that is sufficient to make up the skin, the lips and/or integuments and a liquid continuous fatty phase comprising at least one silicone oil, structured with at least one polymer chosen from homopolymers and copolymers with a weight-average molecular mass ranging from 500 to 500 000, comprising at least one moiety comprising:

at least one polyorganosiloxane group comprising from 1 to 1 000 organosiloxane units in the chain of the moiety or in the form of a graft, and at least two groups capable of establishing hydrogen interactions, chosen from ester, amide, sulphonamide, urethane, carbamate, thiocarbamate, urea, thiourea, oxamido, guanidino and biguanidino groups, and combinations thereof, on condition that at least one of the groups is other than an ester group, the solid particles, the fatty phase and the at least one polymer forming a physiologically acceptable medium.

The invention is illustrated in greater detail in the following examples of makeup formulation comprising a silicone polyamide and at least one pigment and/or at least one filler with a hydrophobic surface. The amounts are given as percentages by mass. The chemical compounds are given mainly as the CTFA name ("International Cosmetic Ingredient Dictionary"). The viscosities indicated are measured at 25° C. at atmospheric pressure.

EXAMPLE 1

Lipstick

| COMPOSITION | |
|---|---|
| Polydimethylsiloxane PDMS (10 cSt) (DC 200-10 cSt from Dow Corning) | qs 100% |
| Phenyltrimethicone (DC 556 from Dow Corning, of 20 cSt) | 12% |
| Hydrogenated isoparaffin (Parleam ® from Nippon Oil Fats) | 5% |
| Hydrophobic treated pigments (red and yellow iron oxides and titanium oxide, treated with perfluoroalkyl phosphate) | 10% |
| Polyethylene wax (Performalen ® 500 from Petrolite) | 12% |
| Silicone polyamide of Example 1 of U.S. Pat. No. 5 981 680 | 15% |
| Preserving agent qs | |
| Fragrance qs | |

The pigments have the following colour indices (CI):
red iron oxide CI: 77491 (95/5)
yellow iron oxide CI: 77492 (95/5)
titanium oxide CI: 77891 (95/5)
95/5 means that there is 95% by weight of oxide and 5% by weight of coating.

This lipstick was obtained by heating the wax and the polymer to the melting point of the mixture, followed by adding the Parleam, some of the phenyltrimethicone and some of the PDMS. Separately, the pigments and the other portion of the silicone oils (PDMS and phenyltrimethicone) were mixed together at room temperature and were then ground in a three-roll mill. This ground material was added to the molten mixture of wax and silicone oils, and the whole was then homogenized. The preserving agent and the fragrance were added, with continued stirring, and the mixture was then cast in a suitable mould.

The product thus obtained has staying power properties, in particular of the colour, and is slippery and non-greasy.

In this Example 1, the used silicone polyamide comprises 30 units [Si(CH$_3$)$_2$—O]. When a silicone polyamide comprising less units [Si(CH$_3$)$_2$—O] than the silicone polyamide of this example is used, a softer and less glossy gel is obtained. In fact, when the number of units [Si(CH$_3$)$_2$—O] of the polymer is increased, a harder and glossy gel is obtained.

EXAMPLE 2

Anhydrous Foundation

| COMPOSITION | |
|---|---|
| PDMS (10 cSt) (DC 200 10 cSt from Dow Corning) | qs 100% |
| Phenyltrimethicone (DC 556) | 12% |
| PDMS (300 cSt) | 5% |
| Hydrophobic treated pigments (red and yellow iron oxides and titanium oxide, treated with perfluoroalkyl phosphate) | 10% |
| Polyethylene wax (Performalen ® 500) | 15% |
| Silicone polyamide of Example 2 of U.S. Pat. No. 5 981 680 | 12% |
| Hydrophobic treated silica (trimethylsiloxyl treatment) | 3% |
| Isononyl isononanoate | 10% |
| Preserving agent qs | |
| Fragrance qs | |

This foundation was prepared as in Example 1, the silica being introduced at the same time as the phenyltrimethicone into the ground pigmentary material, the isononyl isononanoate being introduced into the mixture of wax and of silicone oils.

It has non-greasy, slippery and matt-effect properties and has good staying power over time, in particular of the colour.

The particles used are hydrophobic particles, for example, lipophilic particles.

What is claimed is:

1. A composition comprising a liquid fatty phase comprising at least one silicone oil, structured with a combination comprising:
   1) at least one gelling agent chosen from homopolymers and copolymers with a weight-average molecular mass ranging from 500 to 500 000, comprising at least one moiety comprising:
       at least one polyorganosiloxane group comprising from 1 to 1 000 organosiloxane units in the chain of the moiety or in the form of a graft, and
       at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group,
   the at least one gelling agent being solid at room temperature and soluble in the liquid fatty phase at a temperature of from 25 to 250° C., and
   2) solid particles having a hydrophobic surface, the liquid fatty phase, the at least one gelling agent, and the solid particles forming a physiologically acceptable medium, wherein the solid particles are selected from the group consisting of powders of copolymer of tetrafluoroethylene and of ethylene, powders of copolymer of tetrafluoroethylene and of propylene, polymethylsilsesqioxane powders, particles of lauroyllysine, hydrophilic pigments and fillers grafted with a hydrophobic compound, and mixtures thereof.

2. A composition according to claim 1, wherein the solid particles are chosen from the powders of copolymer of tetrafluoroethylene and of ethylene and the powders of copolymer of tetrafluoroethylene and of propylene.

3. A composition according to claim 1, wherein the solid particles are polymethyl-silsesquioxane powders.

4. A composition according to claim 1, wherein the solid particles are chosen from particles of lauroyllysine.

5. A composition according to claim 1, wherein the solid particles are chosen from hydrophilic pigments and fillers, grafted with a hydrophobic compound.

6. A composition according to claim 5, wherein the hydrophilic pigments are chosen from zinc oxides, iron oxides and titanium oxides.

7. A composition according to claim 5, wherein the hydrophobic compound is a fluoro compound.

8. A composition according to claim 7, wherein the fluoro compound is chosen from perfluoroalkyl monoesters and diesters of phosphoric acid and salts thereof, perfluoropolyethers, perfluorocarboxylic and perfluorosulphonic acids, perfluoroalkyl phosphate salts of diethanolamine, and fluorosilicones.

9. A composition according to claim 5, wherein the hydrophobic compound is a silicon derivative.

10. A composition according to claim 9, wherein the silicon derivative is chosen from reactive silicones initially comprising hydrogenosilane groups, diorganosilanes, alkylalkoxysilanes, silanes comprising a glycidoxypropyl group, polyglycerolated silicones, and silicone-grafted acrylic copolymers and silicone-grafted-polyacrylic copolymers.

11. A composition according to claim 10, wherein the diorganosilanes are chosen from dimethylchlorosilanes.

12. A composition according to claim 5, wherein the hydrophobic compound is chosen from N-acylamino acids, fatty acids and salts thereof, lecithins, and ester oils.

13. A composition according to claim 1, wherein the at least one gelling agent chosen from homopolymers and copolymers comprises at least one moiety corresponding to the formula:

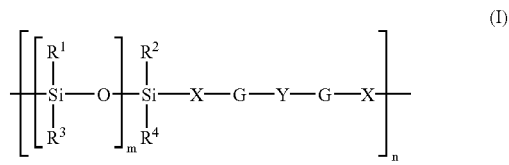

in which:
1) $R^1$, $R^2$, $R^3$ and $R^4$, which may be identical or different, are chosen from:
   linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom,
   $C_6$ to $C_{10}$ aryl groups, optionally substituted with at least one $C_1$ to $C_4$ alkyl group,
   polyorganosiloxane chains optionally comprising at least one atom chosen from oxygen, sulphur and nitrogen;
2) the groups X, which may be identical or different, are chosen from linear and branched $C_1$ to $C_{30}$ alkylenediyl groups, optionally comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
T is chosen from linear and branched, saturated and unsaturated, $C_3$ to $C_{24}$ trivalent and tetravalent hydrocarbon-based groups optionally substituted with a polyorganosiloxane chain, and optionally comprising at lest one atom chosen from O, N and S, or T represents a trivalent atom chosen from N, P and Al, and
$R^5$ is chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;
5) the groups G, which may be identical or different, represent divalent groups chosen from:

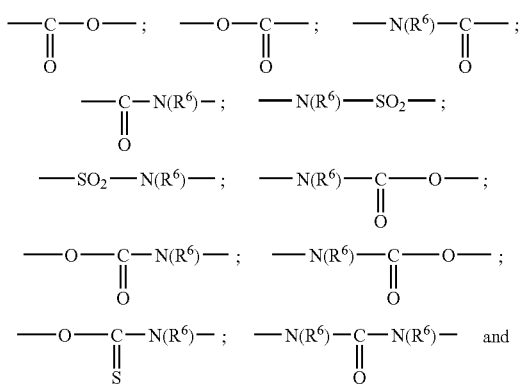

in which $R^6$ is chosen from a hydrogen atom and linear and branched $C_1$ to $C_{20}$ alkyl groups, on condition that at least 50% of the groups $R^6$ of the polymer represents a hydrogen atom and that at least two of the groups G of the polymer are a group other than:

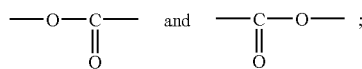

6) n is an integer ranging from 2 to 500, and m is an integer ranging from 1 to 1 000.

14. A composition according to claim 13, wherein n is an integer ranging from 2 to 200.

15. A composition according to claim 13, wherein m is an integer ranging from 1 to 700.

16. A composition according to claim 15, wherein m is an integer ranging from 6 to 200.

17. A composition according to claim 13, wherein Y is chosen from:

a) linear $C_1$ to $C_{20}$ alkylene groups, b) $C_{30}$ to $C_{50}$ branched alkylene groups optionally comprising rings and unconjugated unsaturations, c) $C_5$–$C_6$ cycloalkylene groups, d) phenylene groups optionally substituted with at least one $C_1$ to $C_{40}$ alkyl group, e) $C_1$ to $C_{20}$ alkylene groups comprising from 1 to 5 amide groups, f) $C_1$ to $C_{20}$ alkylene groups comprising at least one substituent chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

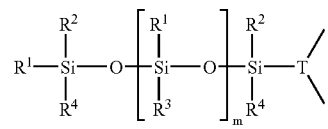

in which $R^1$, $R^2$, $R^3$, $R^4$, T and m are as defined in formula (I) in claim 13, h) polyorganosiloxane chains of formula:

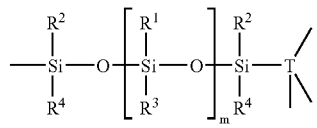

in which $R^1$, $R^2$, $R^3$, $R^4$, T and m are as defined in formula (I) in claim 13.

18. A composition according to claim 1, wherein the at least one gelling agent comprises at least one moiety corresponding to formula (II):

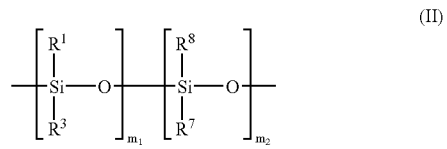

(II)

in which $R^1$ and $R^3$, which may be identical or different, are as defined below, $R^7$ is chosen from a group as defined above for $R^1$ and $R^3$, and a group of formula —X-G-$R^9$ in which X and G are as defined below and $R^9$ is chosen from a hydrogen atom and linear, branched and cyclic, saturated and unsaturated, $C_1$ to $C_{50}$ hydrocarbon-based groups optionally comprising in the chain at least one atom chosen from O, S and N, optionally substituted with at least one fluorine atom and/or at least one hydroxyl group, and a phenyl group optionally substituted with at least one $C_1$ to $C_4$ alkyl group, $R^8$ represents a group of formula —X-G-$R^9$ in which X, G and $R^9$ are as defined above, $m_1$ is an integer ranging from 1 to 998, and m2 is an integer ranging from 2 to 500, in which 1) $R^1$ and $R^3$, which may be identical or different, are chosen from:

linear, branched and cyclic, saturated and unsaturated $C_1$ to $C_{40}$ hydrocarbon- based groups, optionally comprising in the chain at least one atom chosen from oxygen, sulphur and nitrogen, and also optionally being partially or totally substituted with at least one fluorine atom, $C_6$ to $C_{10}$ aryl groups optionally substituted with at least one $C_1$ to $C_4$ alkyl group, polyorganosiloxane chains optionally comprising at least one atom chosen from oxygen, sulphur and nitrogen;

2) the groups X, which may be identical or different, are chosen from linear and branched $C_1$ to $C_{30}$ alkylenediyl groups, optionally comprising in the chain at least one atom chosen from oxygen and nitrogen:

3) the groups G, which may be identical or different, represent divalent grous chosen from:

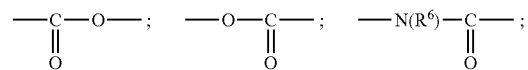

-continued

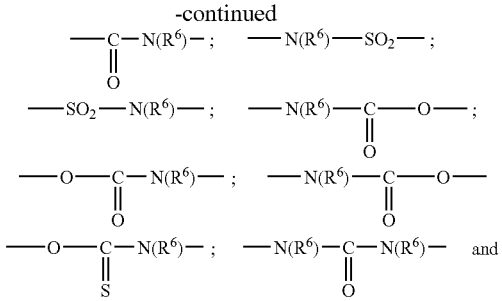

in which $R^6$ is chosen from a hydrogen atom and linear and branched $C_1$ to $C_{20}$ alkyl groups, on condition that at least 50% of the groups $R^6$ of the polymer represents a hydrogen atom and that at least two of the groups G of the polymer are a group other than:

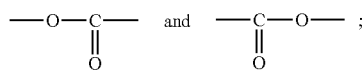

19. A composition according to claim 13, wherein the at least one gelling agent comprises at least one moiety chosen from formulae (III) and (IV):

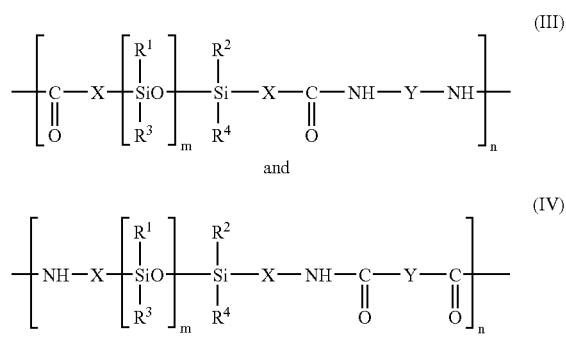

in which $R^1$, $R^2$, $R^3$, $R^4$, X, Y, m and n are as defined in claim 13.

20. A composition according to claim 13, wherein X and/or Y represent an alkylene group comprising in its alkylene portion at least one group chosen from:
1°) 1 to 5 amide, urea and carbamate groups,
2°) $C_5$ and $C_6$ cycloalkyl groups, and
3°) a phenylene group optionally substituted with 1 to 3 identical or different $C_1$ to $C_3$ alkyl groups, and optionally substituted with at least one element chosen from:
a hydroxyl group,
$C_3$ to $C_8$ cycloalkyl groups,
one to three $C_1$ to $C_{40}$ alkyl groups,
a phenyl group optionally substituted with one to three $C_1$ to $C_3$ alkyl groups,
$C_1$ to $C_3$ hydroxyalkyl groups, and $C_1$ to $C_6$ aminoalkyl groups.

21. A composition according to claim 13, wherein Y represents:

in which $R^5$ represents a polyorganosiloxane chain and T represents a group of formula:

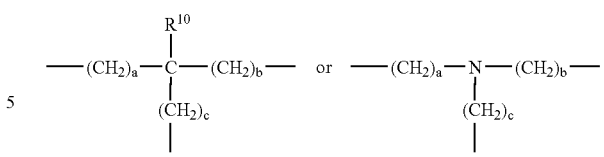

in which a, b and c are, independently, integers ranging from 1 to 10, and $R^{10}$ is chosen from a hydrogen atom and groups defined for $R^1$, $R^2$, $R^3$ and $R^4$ in claim 13.

22. A composition according to claim 13, wherein $R^1$, $R^2$, $R^3$ and $R^4$, which may be identical or different, are chosen from linear and branched $C_1$ to $C_{40}$ alkyl groups, polyorganosiloxane chains and a phenyl group optionally substituted with one to three groups chosen from methyl and ethyl groups.

23. A composition according to claim 22, wherein the linear and branched $C_1$ to $C_{40}$ alkyl groups are chosen from $CH_3$, $C_2H_5$, n-$C_3H_7$ and isopropyl groups.

24. A composition according to claim 1, wherein the at least one gelling agent chosen from homopolymers and copolymers comprises at least one moiety of formula:

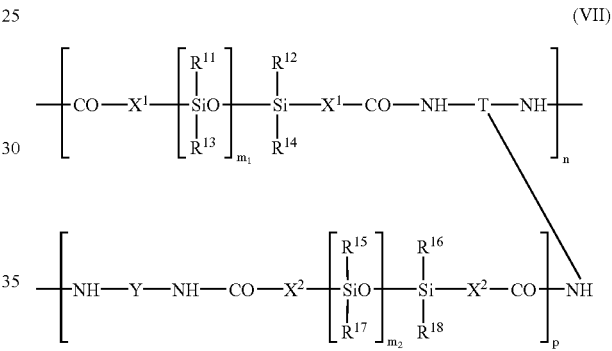

(VII)

in which $X^1$ and $X^2$, wich may be identical or different, have the meaning given for X below, n, Y and T as defined below $R^{11}$ to $R^{18}$ are groups chosen from the same group as $R^1$ to $R^4$ below, $m_1$ and $m_2$ are integers in the range from 1 to 1000, and p is an integer ranging from 2 to 500,
in which
1) $R^1$, $R^2$, $R^3$ and $R^4$, which may be identical or different, are chosen from:
linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom,
$C_6$ to $C_{10}$ aryl groups, optionally substituted with at least one $C_1$ to $C_4$ aryl group,
polyorganosiloxane chains optionally comprising at least one atom chosen from oxygen, sulphur and nitrogen;
2) the group X, which may be identical or different, are chosen from linear and branched $C_1$ to $C_{30}$ alkylenediyl groups, optionaly comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and $R^5$ chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

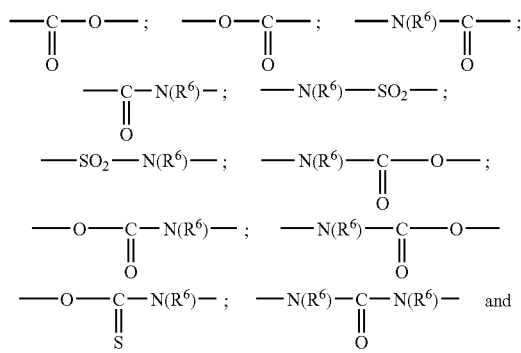

5) n is an integer ranging from 2 to 500.

25. A composition according to claim 24, wherein:

p is in the range from 1 to 25, $R^{11}$ to $R^{18}$ are methyl groups,

T corresponds to one of the following formulae:

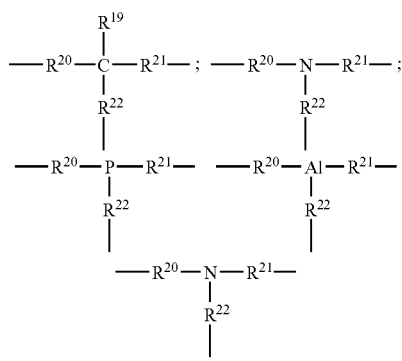

in which $R^{19}$ is chosen from a hydrogen atom and groups chosen from the groups defined for $R^1$ to $R^4$ in claim 13, and $R^{20}$, $R^{21}$ and $R^{22}$ are chosen from linear and branched alkylene groups, $m_1$ and $m_2$ are in the range from 15 to 500, $X^1$ and $X^2$ represent —$(CH_2)_{10}$—, and Y represents —$CH_2$—.

26. A composition according to claim 25, wherein p is in the range from 1 to 7.

27. A composition according to claim 25, wherein T corresponds to the formula:

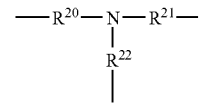

wherein $R^{20}$, $R^{21}$ and $R^{22}$ represent —$CH_2$—$CH_2$—.

28. A composition according to claim 25, wherein $m_1$ and $m_2$ are in the range from 15 to 45.

29. A composition according to claim 1, wherein the at least one gelling agent chosen from homopolymers and copolymers comprises at least one moiety corresponding to the following formula:

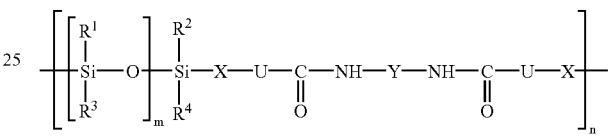

(VIII)

in which $R^1$, $R^2$, $R^3$, $R^4$, X, Y, m and n have the meanings given below, and U is chosen from —O— and —NH—, or Y is chosen from $C_5$ to $C_{12}$ cycloaliphatic and aromatic groups that may be substituted with a group chosen from $C_1$ to $C_{15}$ alkyl groups and $C_5$ to $C_{10}$ aryl groups, or Y is chosen from linear and branched $C_1$ to $C_{40}$ alkylene radicals and $C^4$ to $C_{12}$ cycloalkylene radicals, or Y is chosen from polyurethane and polyurea blocks corresponding to the condensation of several diisocyanate molecules with at least one coupling agent of the diol or diamine type, corresponding to the formula:

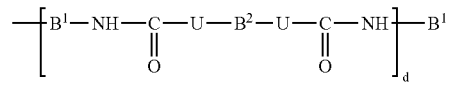

(IX)

in which is a group chosen from the groups given above for Y, U is chosen from —O— and —NH— and $B^2$ is chosen from: linear and branched $C_1$ to $C_{40}$ alkylene groups, which can optionally bear an ionizable group, and neutralizable and quaternizable tertiary amine groups, $C_5$ to $C_{12}$ cycloalkylene groups, optionally bearing alkyl substituents, alkylene groups, and diol radicals, phenylene groups that may optionally bear $C_1$ to $C_3$ alkyl substituents, and groups of formula:

in which T is a hydrocarbon-based trivalent radical optionally comprising at least one hetero atom and $R^5$ is chosen from polyorganosiloxane chains and linear and branched $C_1$ to $C_{50}$ alkyl chains, in which
1) $R^1$, $R^2$, $R^3$, and $R^4$, which may be identical or different, are chosen from:
   linear, branched and cyclic, saturated and unsaturated, $C_1$ to $C_{40}$ hydrocarbon: based groups, optionally comprising in the chain at least one atom chosen from oxygen, sulphur and nitrogen, and also optionally being partially or totally substituted with at least one fluorine atom,
   $C_6$ to $C_{10}$ aryl groups, optionally substituted with at least one $C_1$ to $C_4$ aryl group,
   polyorganosiloxane chains optionally comprising at least one atom chosen from oxygen, sulphur and nitrogen;
2) the group X, which may be identical or different, are chosen from linear and branched $C_1$ to $C_{30}$ alkylenediyl groups, optionaly comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
   T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and A1, and $R^5$ chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

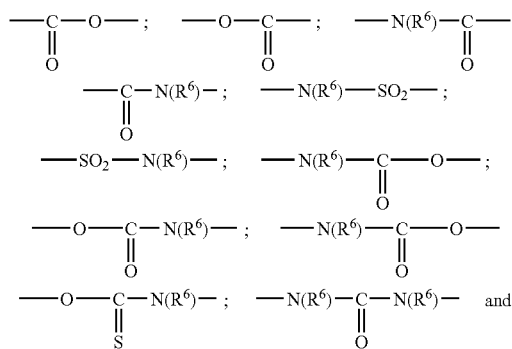

5) n is an integer ranging from 2 to 500, and m is an integer ranging from 1 to 1 000.

30. A composition according to claim 29, wherein Y, which is chosen from $C_5$ to $C_{12}$ cycloaliphatic and aromatic groups that may be substituted with a group chosen from $C_1$ to $C_{15}$ alkyl groups and $C_5$ to $C_{10}$ aryl groups, is a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane.

31. A composition according to claim 29, wherein the ionizable group is chosen from carboxylic acid and sulphonic acid groups.

32. A composition according to claim 29, wherein the alkyl substituents are chosen from one to three groups chosen from methyl and ethyl groups.

33. A composition according to claim 29, wherein the diol radicals are chosen from cyclohexanedimethanol.

34. A composition according to claim 29, wherein the at least one hetero atom is chosen from oxygen, sulphur and nitrogen.

35. A composition according to claim 1, wherein the at least one gelling agent chosen from homopolymers and copolymers comprises at least one moiety of formula:

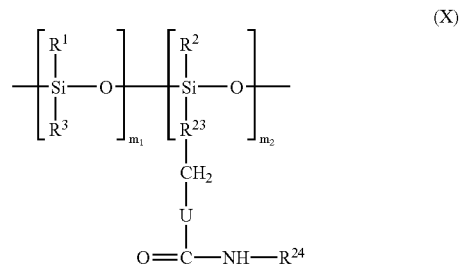

in which $R^1$, $R^2$, $R^3$, $m_1$ and $m_2$ have the meanings given below,

U is chosen from O and NH, $R^{23}$ is chosen from $C_1$ to $C_{40}$ alkylene groups, optionally comprising at least one hetero atom chosen from O and N, and a phenylene group, and $R^{24}$ is chosen from linear, branched and cyclic, saturated and unsaturated $C_1$ to $C_{50}$ alkyl groups, and a phenyl group optionally substituted with one to three $C_1$ to $C_3$ alkyl groups, 1) $R^1$, $R^2$, and $R^3$, which may be identical or different, are chosen from:
   linear, branched and cyclic, saturated and unsaturated, $C_1$ to $C_{40}$ hydrocarbon: based groups, optionally comprising in the chain at least one atom chosen from oxygen, sulphur and nitrogen, and also optionally being partially or totally substituted with at least one fluorine atom,
   $C_6$ to $C_{10}$ aryl groups, optionally substituted with at least one $C_1$ to $C_4$ aryl group,
   polyorganosiloxane chains optionally comprising at least one atom chosen from oxygen, sulphur and nitrogen;

2) $m_1$ and $m_2$ are integers in the range from 1 to 1 000.

36. A composition according to claim 1, wherein the at least one gelling agent chosen from homopolymers and copolymers comprises at least one moiety of formula:

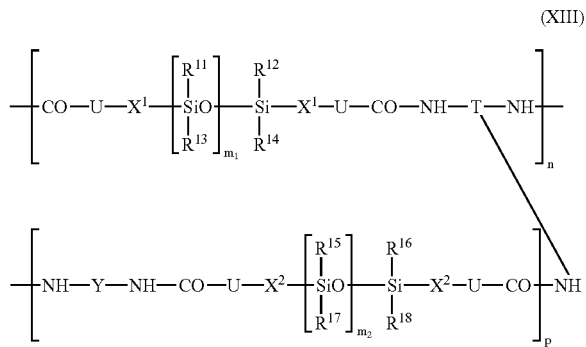

(XIII)

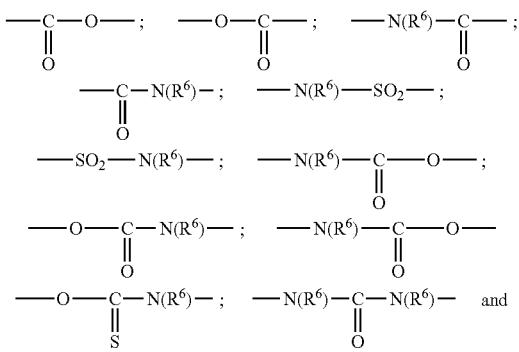

in which $X^1$ and $X^{2,}$ which are identical or different, have the meaning given for X below, n, Y and T are as defined below, $R^{11}$ to $R^{18}$ are groups chosen from the same groups as $R^1$ to $R^4$ below, $m_1$ and $m_2$ are integers in the range from 1 to 1000, and p is an integer ranging from 2 to 500, 1) $R^1$, $R^2$, $R^3$ and $R^4$, which may be identical or different, are chosen from:
  linear, branched and cyclic, saturated and unsaturated, $C_1$ to $C_{40}$ hydrocarbon: based groups, optionally comprising in the chain at least one atom chosen from oxygen, sulphur and nitrogen, and also optionally being partially or totally substituted with at least one fluorine atom,
  $C_6$ to $C_{10}$ aryl groups, optionally substituted with at least one $C_1$ to $C_4$ aryl group,
  polyorganosiloxane chains optionally comprising at least one atom chosen from oxygen, sulphur and nitrogen;

2) the group X, which may be identical or different, are chosen from linear and branched $C_1$ to $C_{30}$ alkylenediyl groups, optionaly comprising in the chain at least one atom chosen from oxygen and nitrogen;

3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which
  T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and $R^5$ chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

5) n is an integer ranging from 2 to 500.

37. A composition according to claim 13, wherein the at least one gelling agent furthermore comprises a hydrocarbon-based moiety comprising two groups capable of establishing hydrogen interactions, chosen from ester, amide, sulphonamide, carbamate, thiocarbamate, urea and thiourea groups.

38. A composition according to claim 37, wherein the at least one gelling agent is chosen from block copolymers and grafted copolymers.

39. A composition according to claim 1, wherein the at least one gelling agent represents from 0.5% to 80% relative to the total weight of the composition, and the solid particles with a hydrophobic surface represent from 0.1% to 90% relative to the total weight of the composition.

40. A composition according to claim 39, wherein the at least one gelling agent represents from 2% to 60% relative to the total weight of the composition.

41. A composition according to claim 40, wherein the at least one gelling agent represents from 5% to 40% relative to the total weight of the composition.

42. A composition according to claim 39, wherein the solid particles with a hydrophobic surface represent from 1% to 70% relative to the total weight of the composition.

43. A composition according to claim 42, wherein the solid particles with a hydrophobic surface represent from 2% to 50% relative to the total weight of the composition.

44. A composition according to claim 1, wherein the liquid fatty phase comprises at least 40% by weight of silicone oil.

45. A composition according to claim 44, wherein the liquid fatty phase comprises at least 50% by weight of silicone oil.

46. A composition according to claim 44, wherein the liquid fatty phase comprises a non-silicone oil.

47. A composition according to claim 1, wherein the liquid fatty phase represents from 5% to 99% of the total weight of the composition.

48. A composition according to claim 47, wherein the liquid fatty phase represents from 20% to 75% of the total weight of the composition.

49. A composition according to claim 1, wherein said composition constitutes a care and/or treatment and/or makeup composition for a keratin material.

50. A composition according to claim 1, wherein said composition further comprises at least one active agent chosen from cosmetic and dermatological active agents.

51. A composition according to claim 1, wherein said composition comprises at least one additive chosen from water, antioxidants, essential oils, preserving agents, fragrances, liposoluble polymers, liquid-fatty-phase gelling agents, waxes, gums, resins, surfactants, and additional cosmetic and dermatological active agents chosen from emollients, moisturizers, vitamins, liquid lanolin, essential fatty acids, lipophilic sunscreens and sunscreens that are soluble in polyols.

52. A composition according to claim 51, wherein the liposoluble polymers are chosen from hydrocarbon-based liposoluble polymers.

53. A composition according to claim 52, wherein the hydrocarbon-based liposoluble polymers are chosen from polyalkylenes and polyvinyl laurate.

54. A composition according to claim 1, wherein said composition is in the form of a transparent anhydrous rigid gel, or in the form of a transparent anhydrous stick.

55. A composition according to claim 1, wherein said composition is in the form of a mascara cake, an eyeliner, a foundation, a lipstick, a blusher, a deodorant product, a makeup-removing product, a makeup product for the body, an eyeshadow, a face powder or a concealer product.

56. A method of limiting the migration of a cosmetic composition or a physiologically acceptable composition, comprising including in said composition a sufficient amount of an anti-migration agent comprising a continuous liquid fatty phase comprising at least one silicone oil, structured with a sufficient amount of at least one polymer chosen from homopolymers and copolymers with a weight-average molecular mass ranging from 500 to 500 000, comprising at least one unit comprising: at least one polyorganosiloxane group comprising from 1 to 1 000 organosiloxafle units in the chain of the moiety or in the form of a graft, and at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group, the at least one polymer being solid at room temperature and soluble in the liquid fatty phase at a temperature of from 25 to 250° C., and solid particles having a hydrophobic surface.

57. A method according to claim 56, wherein the composition has a hardness of from 20 to 900 gf.

58. A method according to claim 57, wherein the composition has a hardness of from 20 to 600 gf.

59. A cosmetic process for limiting the migration of a cosmetic composition, comprising including in said composition a sufficient amount of an anti-migration agent, comprising a liquid fatty phase comprising at least one silicone oil, structured with a sufficient amount of at least one polymer chosen from homopolymers and copolymers with a weight-average molecular mass ranging from 500 to 500 000, comprising at least one moiety comprising:
at least one polyorganosiloxane group comprising from 1 to 1 000 organosiloxane units in the chain of the moiety or in the form of a graft, and
at least two groups capable of establishing hydrogen interactions, chosen from ester, amide, sulphonamide, carbamate, thiocarbamate, urea, thiourea, oxamido, guanidino and biguanidino groups, and combinations thereof, on condition that at least one of the groups is other than an ester group,
the at least one polymer being solid at room temperature and soluble in the liquid fatty phase at a temperature of from 25 to 250° C., and solid particles having a hydrophobic surface.

60. A composition according to claim 17, wherein the linear $C_1$ to $C_{20}$ alkylene groups are chosen from linear $C_1$ to $C_{10}$ alkylene groups.

61. The method according to claim 56, wherein the solid particles are chosen from fillers and pigments.

62. The method according to claim 56, wherein the solid particles are hydrophobic particles, in the form of powders or fibers, or hydrophobic or copolymers chosen from:
 1°) fluoro polymers;
 2°) silicone elastomers;
 3°) polyolefins;
 4°) polyalkyl methacrylates;
 5°) polyamides;
 6°) polystyrenes and polystyrene derivatives;
 7°) polyesters;
 8°) polyacrylics; and
 9°) polyurethanes.

63. The method according to claim 62, wherein the fluoro polymers are chosen from polytetrafluoroethylene powders and powders of copolymer of tetrafluoroethylene and of olefin.

64. The method according to claim 56, wherein the solid particles are chosen from the powders of copolymer of tetrafluoroethylene and of ethylene and the powders of copolymer of tetrafluoroethylene and of propylene.

65. The method according to claim 56, wherein the solid particles are polymethyl-silsesquioxane powders.

66. The method according to claim 56, wherein the solid particles are polyethylene.

67. The method according to claim 56, wherein the solid particles are polymethyl methacrylates.

68. The method according to claim 56, wherein the solid particles are chosen from particles of lauroyllysine and particles of pigments that block out ultraviolet rays.

69. The method according to claim 56, wherein the solid particles are chosen from hydrophilic pigments and fillers, coated with a film of hydrophobic compound or grafted with a hydrophobic compound.

70. The method according to claim 56, wherein the at least one gelling agent chosen from homopolymers and copolymers comprises at least one moiety corresponding to the formula:

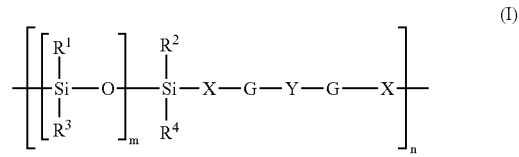

in which:
1) $R^1$, $R^2$, $R^3$ and $R^4$, which may be identical or different, are chosen from:
 linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom,
 $C_6$ to $C_{10}$ aryl groups, optionally substituted with at least one $C_1$ to $C_4$ alkyl group,
 polyorganosiloxane chains optionally comprising at least one atom chosen from oxygen, sulphur and nitrogen;
2) the groups X, which may be identical or different, are chosen from linear and branched $C_1$ to $C_{30}$ alkylenediyl groups, optionally comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which
T is chosen from linear and branched, saturated and unsaturated, $C_3$ to $C_{24}$ trivalent and tetravalent hydrocarbon-based groups optionally substituted with a polyorganosiloxane chain, and optionally comprising at lest one atom chosen from O, N and S, or T represents a trivalent atom chosen from N, P and Al, and $R^5$ is chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

5) the groups G, which may be identical or different, represent divalent groups chosen from:

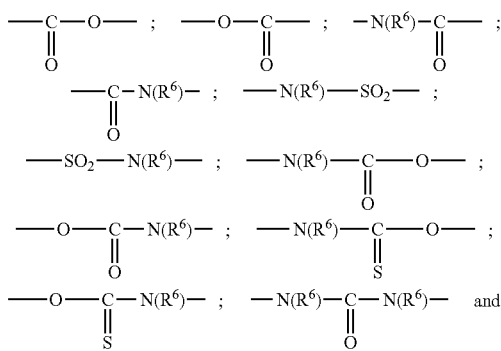

in which $R^6$ is chosen from a hydrogen atom and linear and branched $C_1$ to $C_{20}$ alkyl groups, on condition that at least 50% of the groups $R^6$ of the polymer represents a hydrogen atom and that at least two of the groups G of the polymer are a group other than:

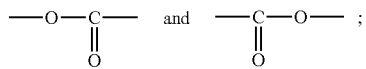

6) n is an integer ranging from 2 to 500, and m is an integer ranging from 1 to 1 000.

71. The method according to claim 70, wherein n is an integer ranging from 2 to 200.

72. The method according to claim 70, wherein m is an integer ranging from 1 to 700.

73. The method according to claim 72, wherein m is an integer ranging from 6 to 200.

74. The method according to claim 70, wherein Y is chosen from:

a) linear $C_1$ to $C_{20}$ alkylene groups,
b) $C_{30}$ to $C_{50}$ branched alkylene groups optionally comprising rings and unconjugated unsaturations,
c) $C_5$–$C_6$ cycloalkylene groups,
d) phenylene groups optionally substituted with at least one $C_1$ to $C_{40}$ alkyl group,
e) $C_1$ to $C_{20}$ alkylene groups comprising from 1 to 5 amide groups,
f) $C_1$ to $C_{20}$ alkylene groups comprising at least one substituent chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

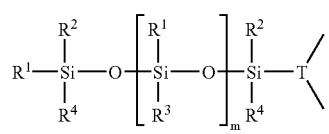

in which $R^1$, $R^2$, $R^3$, $R^4$, T and m are as defined in formula (I) in claim 70.

h) polyorganosiloxane chains of formula:

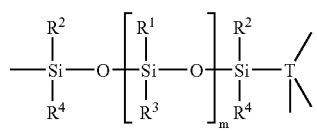

in which $R^1$, $R^2$, $R^3$, $R^4$, T and m are as defined in fommla (I) in claim 70.

75. The method according to claim 56, wherein the at least one gelling agent comprises at least one moiety corresponding to formula (II):

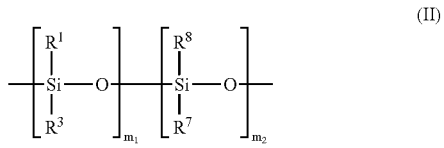

(II)

in which
$R^1$ and $R^3$, which may be identical or different, are as defined below,
$R^7$ is chosen from a group as defined above for $R^1$ and $R^3$, and a group of formula —X-G-$R^9$ in which X and G are as defined below and $R^9$ is chosen from a hydrogen atom and linear, branched and cyclic, saturated and unsaturated, $C_1$ to $C_{50}$ hydrocarbon-based groups optionally comprising in the chain at least one atom chosen from O, S and N, optionally substituted with at least one fluorine atom and/or at least one hydroxyl group, and a phenyl group optionally substituted with at least one $C_1$ to $C_4$ alkyl group,
$R^8$ represents a group of formula —X-G-$R^9$ in which X, G and $R^9$ are as defined above,
$m_1$ is an integer ranging from 1 to 998, and
m2 is an integer ranging from 2 to 500,
in which
1) $R^1$, and $R^3$, which may be identical or different, are chosen from:
linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom, $C_6$ to $C_{10}$ aryl groups, optionally substituted with at least one $C_1$ to $C_4$ alkyl group, polyorganosiloxane chains optionally comprising at least one atom chosen from oxygen, sulphur and nitrogen;

2) the groups X, which may be identical or different, are chosen from linear and branched $C_1$ to $C_{30}$ alkylenediyl groups, optionally comprising in the chain at least one atom chosen from oxygen and nitrogen;

3) the groups G, which may be identical or different, represent divalent groups chosen from:

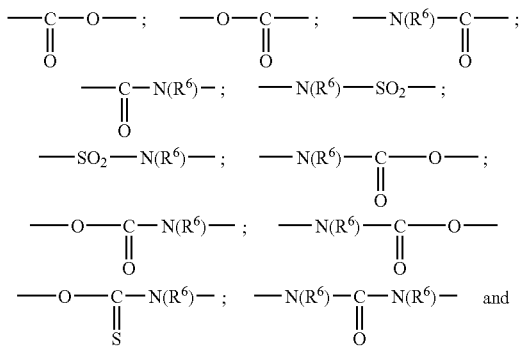

in which $R^6$ is chosen from a hydrogen atom and linear and branched $C_1$ to $C_{20}$ alkyl groups, on condition that at least 50% of the groups $R^6$ of the polymer represents a hydrogen atom and that at least two of the groups G of the polymer are a group other than:

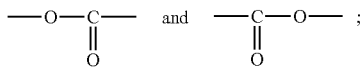

76. The method according to claim 70, wherein the at least one gelling agent comprises at least one moiety chosen from formulae (III) and (IV):

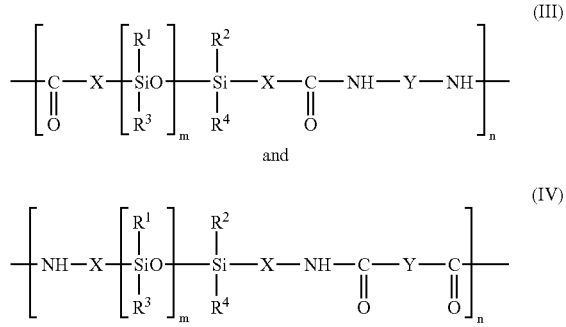

in which $R^1$, $R^2$, $R^3$, $R^4$, X, Y, m and n are as defined in claim 70.

77. The method according to claim 70, wherein X and/or Y represent an alkylene group comprising in its alkylene portion at least one group chosen from:

1°) 1 to 5 amide, urea and carbamate groups,
2°) $C_5$ and $C_6$ cycloalkyl groups, and
3°) a phenylene group optionally substituted with 1 to 3 identical or different $C_1$ to $C_3$ alkyl groups, and optionally substituted with at least one element chosen from:

a hydroxyl group,
$C_3$ to $C_8$ cycloalkyl groups,
one to three $C_1$ to $C_{40}$ alkyl groups,
a phenyl group optionally substituted with one to three $C_1$ to $C_3$ alkyl groups,
$C_1$ to $C_3$ hydroxyalkyl groups, and $C_1$ to $C_6$ aminoalkyl groups.

78. The method according to claim 70, wherein Y represents:

in which $R^5$ represents a polyorganosiloxane chain and T represents a group of formula:

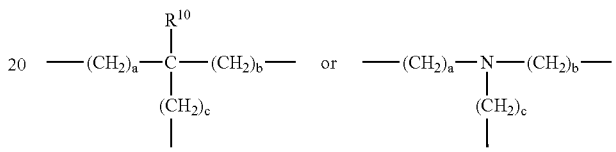

in which a, b and c are, independently, integers ranging from 1 to 10, and $R^{10}$ is chosen from a hydrogen atom and groups defined for $R^1$, $R^2$, $R^3$ and $R^4$ in claim 70.

79. The method according to claim 70, wherein $R^1$, $R^2$, $R^3$ and $R^4$, which may be identical or different, are chosen from linear and branched $C_1$ to $C_{40}$ alkyl groups, polyorganosiloxane chains and a phenyl group optionally substituted with one to three groups chosen from methyl and ethyl groups.

80. The method according to claim 79, wherein the linear and branched $C_1$ to $C_{40}$ alkyl groups are chosen from $CH_3$, $C_2H_5$, n-$C_3H_7$ and isopropyl groups.

81. The method according to claim 56, wherein the at least one gelling agent chosen from homopolymers and copolymers comprises at least one moiety of formula:

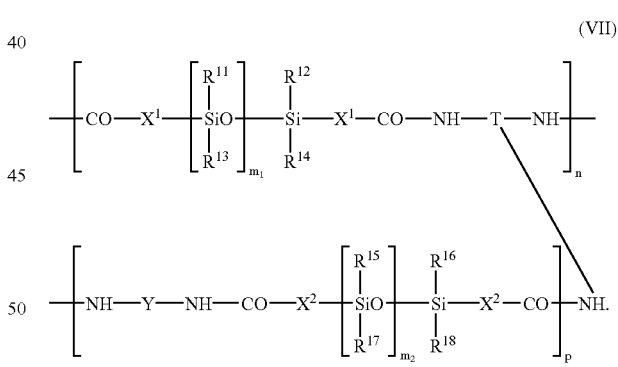

in which $X^1$ and $X^2$, which may be identical or different, have the meaning given for X below, n, Y and T are as defined below, $R^{11}$ to $R^{18}$ are groups chosen from the same group as $R^1$ to $R^4$ of below, $m_1$ and $m_2$ are integers in the range from 1 to 1 000, and p is an integer ranging from 2 to 500, 1) $R^1$, $R^2$, $R^3$, and $R^4$, which may be identical or different, are chosen from:

linear, branched and cyclic, saturated and unsaturated, $C_1$ to $C_{40}$ hydrocarbon-based groups, optionally comprising in the chain at least one atom chosen from oxygen, sulphur and nitrogen, and also optionally being partially or totally substituted with at least one fluorine atom, $C_6$ to $C_{10}$ aryl groups, optionally substituted with at least one $C_1$ to $C_4$ aryl group, polyorganosiloxane chains optionally comprising at least one atom chosen from oxygen, sulphur and nitrogen;

2) the group X, which may be identical or different, are chosen from linear and branched $C_1$ to $C_{30}$ alkylenediyl groups, optionaly comprising in the chain at least one atom chosen from oxygen and nitrogen;

3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and $R^5$ chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

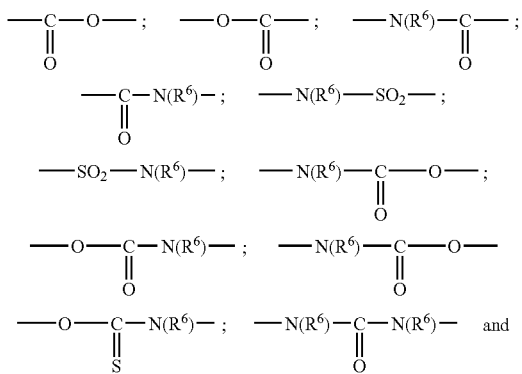

5) n is an integer ranging from 2 to 500.

82. The method according to claim 81, wherein:

p is in the range from 1 to 25, $R^{11}$ to $R^{18}$ are methyl groups,

T corresponds to one of the following formulae:

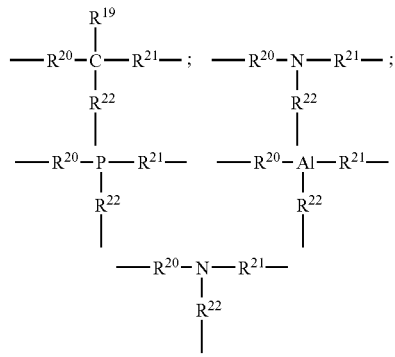

in which $R^{19}$ is chosen from a hydrogen atom and groups chosen from the groups defined for $R^1$ to $R^4$ in claim 70, and $R^{20}$, $R^{21}$ and $R^{22}$ are chosen from linear and branched alkylene groups, $m_1$ and $m_2$ are in the range from 15 to 500, $X^1$ and $X^2$ represent —$(CH_2)_{10}$—, and Y represents —$CH_2$—.

83. The method according to claim 82, wherein p is in the range from 1 to 7.

84. The method according to claim 82, wherein T corresponds to the formula:

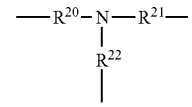

wherein $R^{20}$, $R^{21}$ and $R^{22}$ represent —$CH_2$—$CH_2$—.

85. The method according to claim 82, wherein $m_1$ and $m_2$ are in the range from 15 to 45.

86. The method according to claim 56, the at least one gelling agent chosen from homopolymers and copolymers comprises at least one moiety corresponding to the following formula:

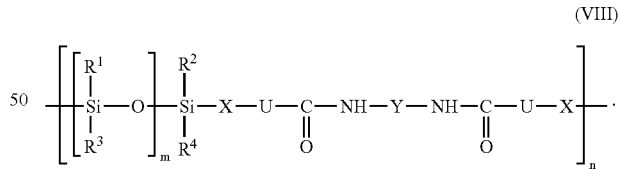

(VIII)

in which $R^1$, $R^2$, $R^3$, $R^4$, X, Y, m and n have the meanings given below, and U is chosen from —O— and —NH—, or Y is chosen from $C_5$ to $C_{12}$ cycloaliphatic and aromatic groups that maybe substituted with a group chosen from $C_1$ to $C_{15}$ alkyl groups and $C_5$ to $C_{10}$ aryl groups, or Y is chosen from linear and branched $C_1$ to $C_{40}$ alkylene radicals and $C^4$ to $C_{12}$ cycloalkylene radicals, or Y is chosen from polyurethane and polyurea blocks corresponding to the condensation of several diisocyanate molecules with at least one coupling agent of the diol or diamine type, corresponding to the formula:

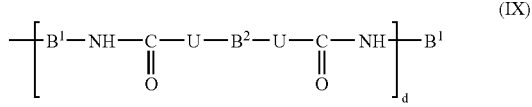

(IX)

in which B¹ is a group chosen from the groups given above for Y, U is chosen from —O— and —NH— and B² is chosen from: linear and branched $C_1$ to $C_{40}$ alkylene groups, which can optionally bear an ionizable group, and neutralizable and quaternizable tertiary amine groups, $C_5$ to $C_{12}$ cycloalkylene groups, optionally bearing alkyl substituents, alkylene groups, and diol radicals, phenylene groups that may optionally bear $C_1$ to $C_3$ alkyl substituents, and groups of formula:

in which T is a hydrocarbon-based trivalent radical optionally comprising at least one hetero atom and $R^5$ is chosen from polyorganosiloxane chains and linear and branched $C_1$ to $C_{50}$ alkyl chains, 1) $R^1$, $R^2$, $R^3$, and $R^4$, which may be identical or different, are chosen from:
   linear, branched and cyclic, saturated and unsaturated, $C_1$ to $C_{40}$ hydrocarbon: based groups, optionally comprising in the chain at least one atom chosen from oxygen, sulphur and nitrogen, and also optionally being partially or totally substituted with at least one fluorine atom,
   $C_6$ to $C_{10}$ aryl groups, optionally substituted with at least one $C_1$ to $C_4$ aryl group,
   polyorganosiloxane chains optionally comprising at least one atom chosen from oxygen, sulphur and nitrogen;
2) the group X, which may be identical or different, are chosen from linear and branched $C_1$ to $C_{30}$ alkylenediyl groups, optionaly comprising in the chain at least one atom chosen from oxygen and nitrogen;
3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
   T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and Al, and $R^5$ chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

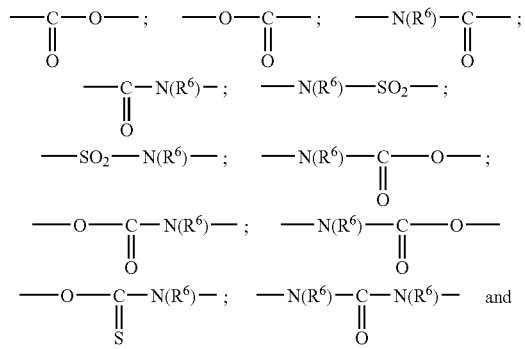

5) n is an integer ranging from 2 to 500, and m is an integer ranging from 1 to 1 000.

87. The method according to claim 86, wherein Y, which is chosen from $C_5$ to $C_{12}$ cycloaliphatic and aromatic groups that may be substituted with a group chosen from $C_1$ to $C_{15}$ alkyl groups and $C_5$ to $C_{10}$ aryl groups, is a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane.

88. The method according to claim 86, wherein the ionizable group is chosen from carboxylic acid and sulphonic acid groups.

89. The method according to claim 86, wherein the alkyl substituents are chosen from one to three groups chosen from methyl and ethyl groups.

90. The method according to claim 86, wherein the diol radicals are chosen from cyclohexanedimethanol.

91. The method according to claim 86, wherein the at least one hetero atom is chosen from oxygen, sulphur and nitrogen.

92. The method according to claim 56, wherein the at least one gelling agent chosen from homopolymers and copolymers comprises at least one moiety of formula:

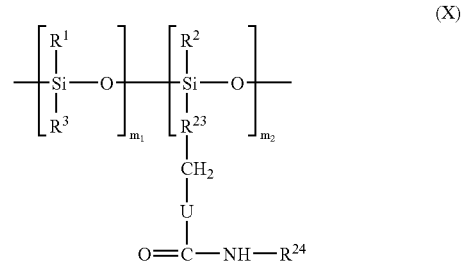

(X)

in which $R^1$, $R^2$, $R^3$, $m_1$ and $m_2$ have the meanings given below,
   U is chosen from O and NH,
   $R^{23}$ is chosen from $C_1$ to $C_{40}$ alkylene groups, optionally comprising at least one hetero atom chosen from O and N, and a phenylene group, and
   $R^{24}$ is chosen from linear, branched and cyclic, saturated and unsaturated $C_1$ to $C_{50}$ alkyl groups, and a phenyl group optionally substituted with one to three $C_1$ to $C_3$ alkyl groups, 1) $R^1$, $R^2$ and $R^3$, which may be identical or different, are chosen from:

linear, branched and cyclic, saturated and unsaturated, $C_1$ to $C_{40}$ hydrocarbon: based groups, optionally comprising in the chain at least one atom chosen from oxygen, sulphur and nitrogen, and also optionally being partially or totally substituted with at least one fluorine atom, $C_6$ to $C_{10}$ aryl groups, optionally substituted with at least one $C_1$ to $C_4$ aryl group, polyorganosiloxane chains optionally comprising at least one atom chosen from oxygen, sulphur and nitrogen;

2) $m_1$ and $m_2$ are integers in the range from 1 to 1 000.

93. The method according to claim 56, wherein the at least one gelling agent chosen from homopolymers and copolymers comprises at least one moiety of formula:

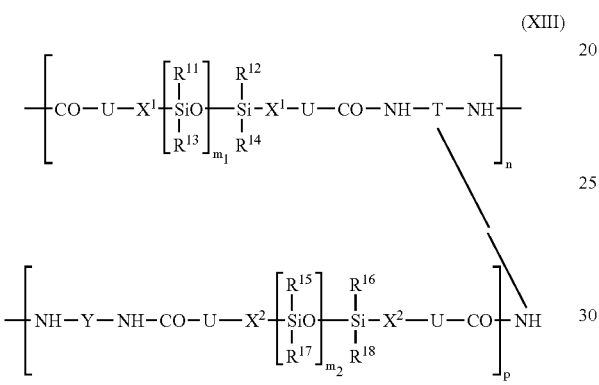

(XIII)

in which $X^1$ and $X^2$, which are identical or different, have the meaning given for X below, n, Y and T are as defined below, $R^{11}$ to $R^{18}$ are groups chosen from the same groups as $R^1$ to $R^4$ below, $m_1$ and $m_2$ are integers in the range from 1 to 1 000, and p is an integer ranging from 2 to 500, in which 1) $R^1$, $R^2$, $R^3$, and $R^4$, which may be identical or different, are chosen from:

linear, branched and cyclic, saturated and unsaturated, $C_1$ to $C_{40}$ hydrocarbon: based groups, optionally comprising in the chain at least one atom chosen from oxygen, sulphur and nitrogen, and also optionally being partially or totally substituted with at least one fluorine atom, $C_6$ to $C_{10}$ aryl groups, optionally substituted with at least one $C_1$ to $C_4$ aryl group, polyorganosiloxane chains optionally comprising at least one atom chosen from oxygen, sulphur and nitrogen;

2) the group X, which may be identical or different, are chosen from linear and branched $C_1$ to $C_{30}$ alkylenediyl groups, optionaly comprising in the chain at least one atom chosen from oxygen and nitrogen;

3) Y is chosen from saturated and unsaturated, $C_1$ to $C_{50}$ linear and branched divalent alkylene, arylene, cycloalkylene, alkylarylene and arylalkylene groups, optionally comprising at least one atom chosen from oxygen, sulphur and nitrogen, and optionally substituted by one of the following atoms and groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T is chosen from linear and branched, saturated and unsaturated, $C_3$ to $C_{24}$ trivalent and tetravalent hydrocarbon-based groups optionally substituted with a polyorganosiloxane chain, and optionally comprising at least one atom chosen from O, N and S, or T represents a trivalent atom chosen from N, P and A1, and $R^5$ chosen from linear and branched $C_1$ to $C_{50}$ alkyl groups and polyorganosiloxane chains, optionally comprising at least one group chosen from ester, amide, urethane, thiocarbamate, urea, thiourea and sulphonamide groups, which may optionally be linked to another chain of the polymer;

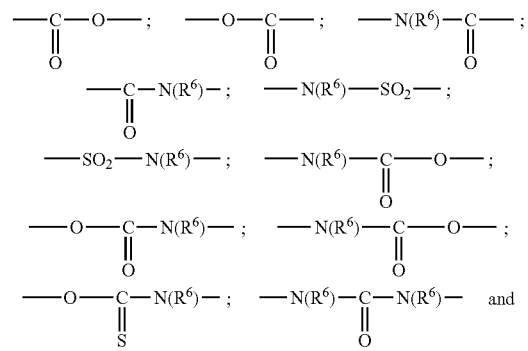

5) n is an integer ranging from 2 to 500.

94. The method according to claim 70, wherein the at least one gelling agent furthermore comprises a hydrocarbon-based moiety comprising two groups capable of establishing hydrogen interactions, chosen from ester, amide, sulphonamide, carbamate, thiocarbamate, urea and thiourea groups.

95. The method according to claim 94, wherein the at least one gelling agent is chosen from block copolymers and grafted copolymers.

96. The method according to claim 56, wherein the at least one gelling agent represents from 0.5% to 80% relative to the total weight of the composition, and the solid particles with a hydrophobic surface represent from 0.1% to 90% relative to the total weight of the composition.

97. The method according to claim 96, wherein the at least one gelling agent represents from 2% to 60% relative to the total weight of the composition.

98. The method according to claim 97, wherein the at least one gelling agent represents from 5% to 40% relative to the total weight of the composition.

99. The method according to claim 96, wherein the solid particles with a hydrophobic surface represent from 1% to 70% relative to the total weight of the composition.

100. The method according to claim 99, wherein the solid particles with a hydrophobic surface represent from 2% to 50% relative to the total weight of the composition.

101. The method according to claim 56, wherein said composition further comprises at least one active agent chosen from cosmetic and dermatological active agents.

102. The method according to claim 56, wherein said composition is in the form of a mascara cake, an eyeliner, a foundation, a lipstick, a blusher, an eyeshadow, a face powder or a concealer product.

* * * * *

UNITED STATES PATENT AND TRADEMARK OFFICE
CERTIFICATE OF CORRECTION

PATENT NO.         : 7,078,026 B2
APPLICATION NO. : 10/170549
DATED               : July 18, 2006
INVENTOR(S)        : Veronique Ferrari et al.

It is certified that error appears in the above-identified patent and that said Letters Patent is hereby corrected as shown below:

Column 34, line 49, "in which is a group" should read --in which $B^1$ is a group--.

Column 35, line 42, "$R^5$ chosen" should read --$R^5$ is chosen--.

Column 45, line 2, "$C_1$ to $C_4$ aryl group" should be --$C_1$ to $C_4$ alkyl group--.

Column 47, line 36, "$C_1$ to $C_4$ aryl group" should be --$C_1$ to $C_4$ alkyl group--.

Column 49, line 10, "$C_1$ to $C_4$ aryl group" should be --$C_1$ to $C_4$ alkyl group--;

line 50, "$C_1$ to $C_4$ aryl group" should be --$C_1$ to $C_4$ alkyl group--.

Column 50, line 19, "$R^5$ chosen" should read --$R^5$ is chosen--.

Signed and Sealed this

Sixteenth Day of January, 2007

JON W. DUDAS
*Director of the United States Patent and Trademark Office*